US009787965B2

(12) United States Patent
Tozuka et al.

(10) Patent No.: US 9,787,965 B2
(45) Date of Patent: Oct. 10, 2017

(54) CAMERA SYSTEM, COLOR CONVERSION DEVICE AND METHOD EMPLOYED THEREUPON, AND RECORDING MEDIUM FOR COLOR CONVERSION PROGRAM

(71) Applicant: FUJIFILM Corporation, Tokyo (JP)

(72) Inventors: Koichi Tozuka, Ashigara-kami-gun (JP); Hideyasu Ishibashi, Ashigara-kami-gun (JP); Ryusuke Osanai, Ashigara-kami-gun (JP); Naoko Yoshida, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 300 days.

(21) Appl. No.: 14/707,565

(22) Filed: May 8, 2015

(65) Prior Publication Data
US 2015/0245009 A1    Aug. 27, 2015

Related U.S. Application Data

(63) Continuation of application No. PCT/JP2013/080251, filed on Nov. 8, 2013.

(30) Foreign Application Priority Data

Nov. 9, 2012   (JP) ................... 2012-247895
Jul. 31, 2013  (JP) ................... 2013-158950

(51) Int. Cl.
*H04N 13/02*  (2006.01)
*H04N 13/00*  (2006.01)
(Continued)

(52) U.S. Cl.
CPC ....... *H04N 13/0037* (2013.01); *A61B 5/1032* (2013.01); *A61C 19/04* (2013.01);
(Continued)

(58) Field of Classification Search
CPC .. H04N 13/0037; H04N 1/6086; H04N 9/643; H04N 9/735; H04N 13/0257; A61B 5/1032; G06T 7/90
See application file for complete search history.

(56) References Cited

U.S. PATENT DOCUMENTS 4,758,085 A      7/1988 Lequime et al.
5,864,364 A *    1/1999 Ohyama ............ H04N 1/6088
                                                    348/14.08
(Continued)

FOREIGN PATENT DOCUMENTS

EP    1 207 386 A1    5/2002
EP    1 253 554 A2   10/2002
(Continued)

OTHER PUBLICATIONS

Arzate-Vázquez et al., "Image Processing Applied to Classification of Avocado Variety Hass (*Persea americana* Mill) During the Ripening Process", Food Bioprocess Technol vol. 4, 2011, (Published online May 17, 2011), pp. 1307-1313.
(Continued)

*Primary Examiner* — Mishawn Hunter
(74) *Attorney, Agent, or Firm* — Birch, Stewart, Kolasch & Birch, LLP

(57) ABSTRACT

A camera system includes: a database which stores a plurality of stereoscopic color profiles, in which conversion relationships calculated from second image data obtained by photographing a plurality of reference color stereoscopic objects assigned with reference colorimetric values in advance and the reference colorimetric values corresponding to the second image data are associated with a plurality of illumination conditions in photographing; a selection unit which, based on an illumination condition at the time of photographing of a stereoscopic subject, selects a stereoscopic color profile corresponding to the illumination con-
(Continued)

dition; and a color conversion unit which performs color conversion from first image data of a photographed image of the stereoscopic subject to colorimetric values, based on the selected stereoscopic color profile.

29 Claims, 8 Drawing Sheets

(51) Int. Cl.
| | |
|---|---|
| *H04N 1/60* | (2006.01) |
| *G01J 3/50* | (2006.01) |
| *H04N 9/73* | (2006.01) |
| *G01J 3/52* | (2006.01) |
| *A61C 19/04* | (2006.01) |
| *G06T 11/00* | (2006.01) |
| *A61B 5/103* | (2006.01) |
| *H04N 9/64* | (2006.01) |
| *G06T 7/90* | (2017.01) |
| *A61B 5/00* | (2006.01) |

(52) U.S. Cl.
CPC .............. *G01J 3/508* (2013.01); *G01J 3/52* (2013.01); *G01J 3/524* (2013.01); *G06T 7/90* (2017.01); *G06T 11/001* (2013.01); *H04N 1/6086* (2013.01); *H04N 9/643* (2013.01); *H04N 9/735* (2013.01); *H04N 13/0257* (2013.01); *A61B 5/0077* (2013.01); *A61B 5/0088* (2013.01); *A61B 5/441* (2013.01); *G06T 2207/10024* (2013.01); *G06T 2207/30036* (2013.01)

(56) References Cited

U.S. PATENT DOCUMENTS

| | | | |
|---|---|---|---|
| 6,210,159 B1* | 4/2001 | Lehmann | A61C 19/00 356/408 |
| 7,756,327 B2 | 7/2010 | Komiya et al. | |
| 7,830,566 B2* | 11/2010 | Yamada | H04N 9/735 358/1.9 |
| 7,876,955 B2 | 1/2011 | Komiya et al. | |
| 2006/0001739 A1* | 1/2006 | Babayoff | A61B 1/00009 348/49 |
| 2006/0250668 A1* | 11/2006 | Komiya | G01J 3/46 358/504 |
| 2008/0192235 A1 | 8/2008 | Komiya et al. | |
| 2012/0300050 A1* | 11/2012 | Korichi | A61B 5/0059 348/77 |

FOREIGN PATENT DOCUMENTS

| | | |
|---|---|---|
| FR | 2 588 656 A1 | 4/1987 |
| JP | 4-367658 A | 12/1992 |
| WO | WO 2004/036162 A1 | 4/2004 |

OTHER PUBLICATIONS

Extended European Search Report dated Jun. 10, 2016 for Application No. 13853936.6.
International Preliminary Report on Patentability and Written Opinion of the International Searching Authority (Forms PCT/IB/338, PCT/IB/373 and PCT/ISA/237), dated May 21, 2015, for International Application No. PCT/JP2013/080251.
International Search Report issued in PCT/JP2013/080251, dated Dec. 3, 2013.
Chinese Office Action, dated Jun. 2, 2017, for corresponding Chinese Application No. 201380061073.5, with English translation.

\* cited by examiner

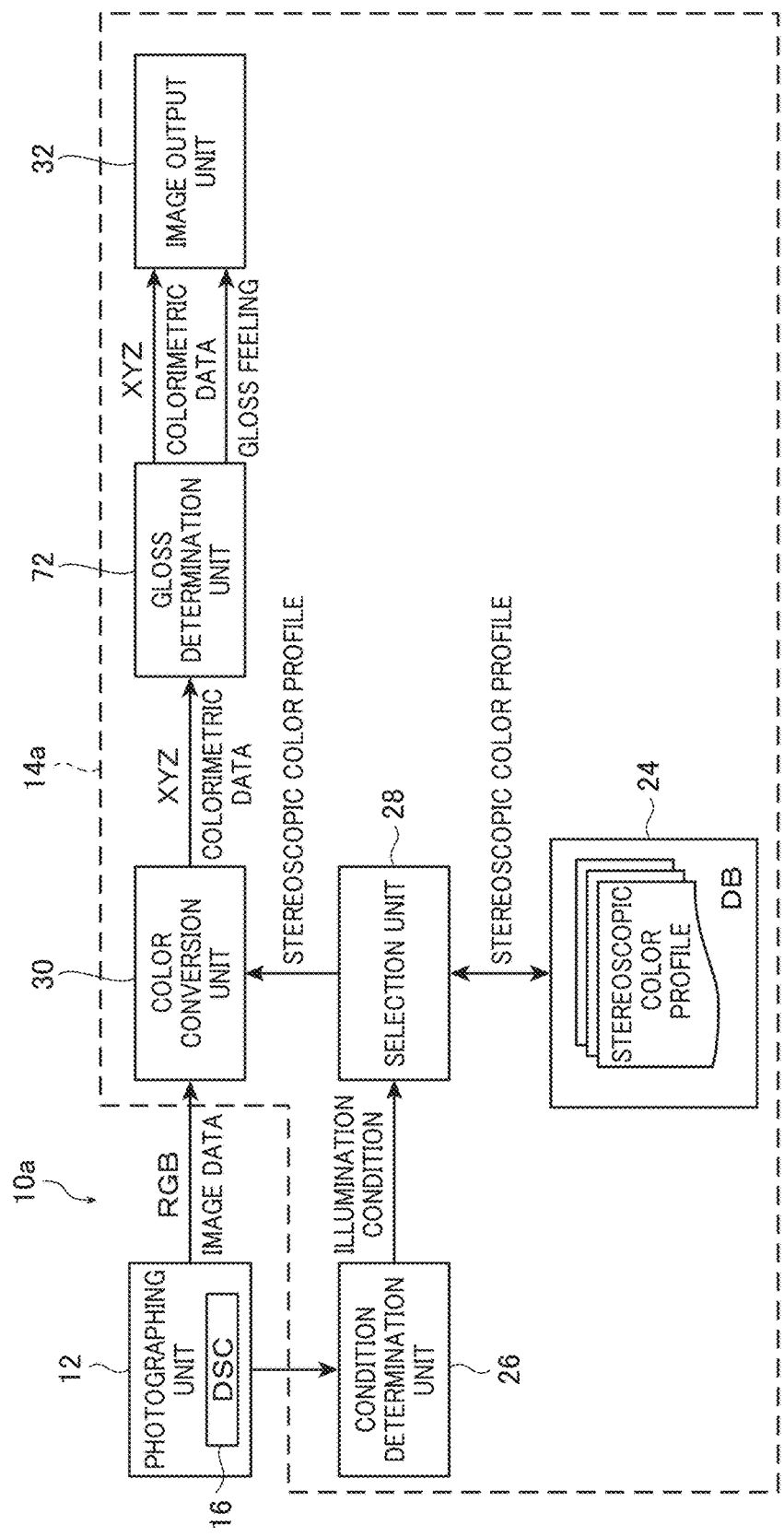

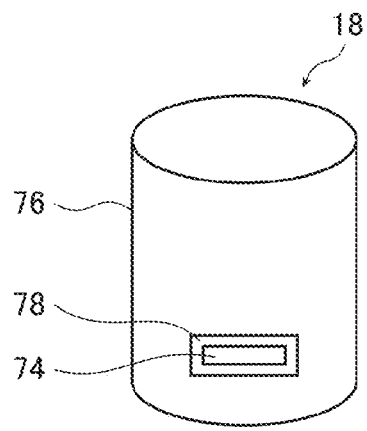 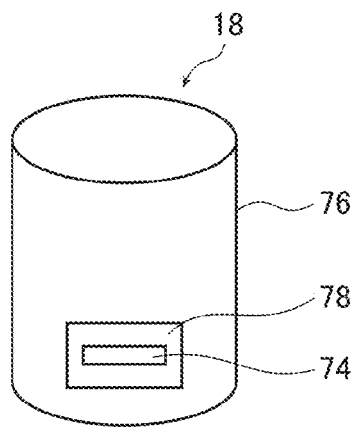
FIG. 10A  FIG. 10B
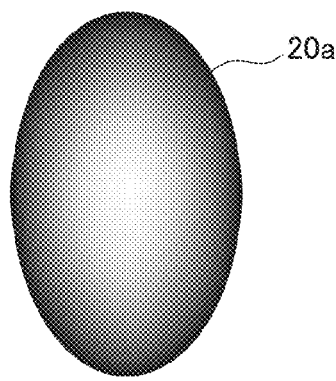 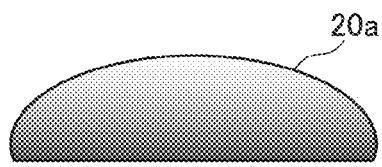
FIG. 11A  FIG. 11B
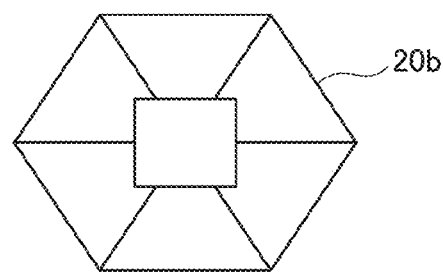
FIG. 11C FIG. 12
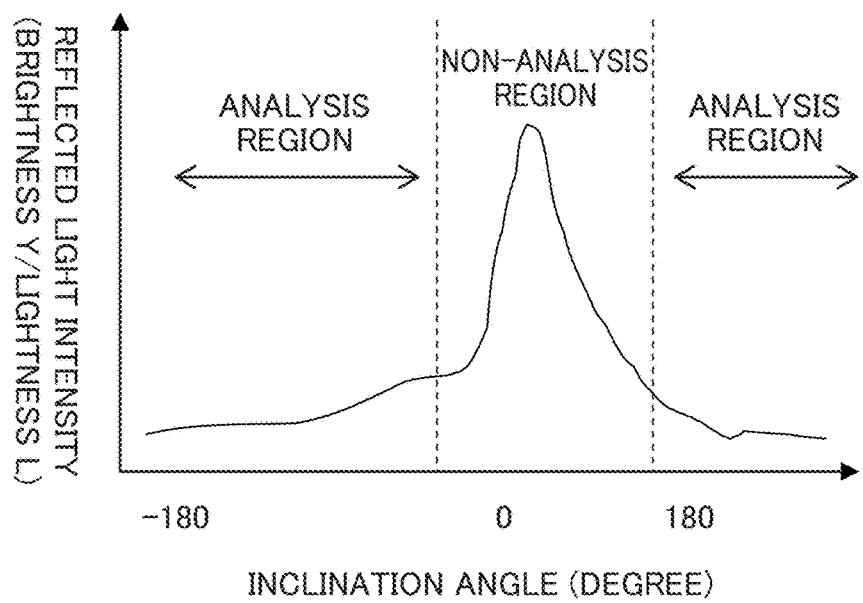
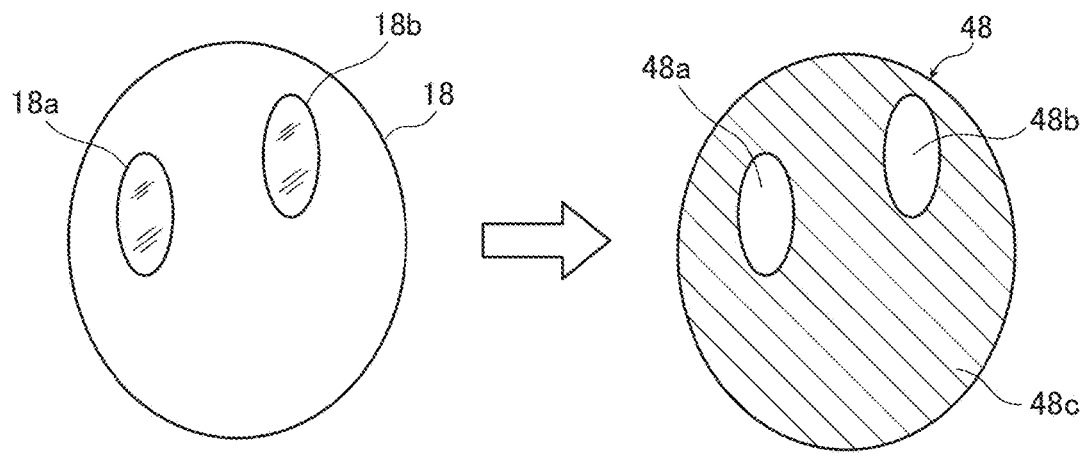
FIG. 13A          FIG. 13B

CAMERA SYSTEM, COLOR CONVERSION DEVICE AND METHOD EMPLOYED THEREUPON, AND RECORDING MEDIUM FOR COLOR CONVERSION PROGRAM

CROSS-REFERENCE TO RELATED APPLICATIONS

This application is a Continuation of PCT International Application No. PCT/JP2013/080251 filed on Nov. 8, 2013, which claims priority under 35 U.S.C. §119(a) to Japanese Patent Application No. 2012-247895 filed on Nov. 9, 2012 and Japanese Patent Application No. 2013-158950 filed on Jul. 31, 2013. Each of the above application(s) is hereby expressly incorporated by reference, in its entirety, into the present application.

BACKGROUND OF THE INVENTION

The present invention relates to a camera system, such as a dental camera system or a skin measuring (diagnostic) camera system, a color conversion device, a color conversion method, and a recording medium for a color conversion program, and in particular, to a color conversion device and method which processes a photographed image photographed by a digital camera, such as a digital still camera (DSC) or a digital video camera, and outputs a colorimetric image, a camera system provided with a photographing unit including the color conversion device and the digital camera, and a computer-readable recording memory or medium in which is stored a color conversion program which executes the color conversion method.

Conventionally, in dentistry, when supplementing a chipped tooth with a denture or a bridge, an artificial tooth or a dental prosthesis is used. The artificial tooth or the dental prosthesis is made of an acrylic resin, dental porcelain, or the like, but it is necessary to select an artificial tooth or a dental prosthesis with a color tone conforming to a tooth of a patient. Accordingly, a color reference (color sample) called a shade guide which is a complete set of a plurality of numbered samples having different color tones is used. The selection of the color tone and the specification of the number in the color reference are performed at a well-lit window with no direct sunlight without using illumination. A dental technician prepares an artificial tooth or a dental prosthesis such that it has a color tone of a number specified by a dentist.

In dentistry described above, a method is also performed in which a color reference such as a shade guide, and a subject such as a tooth of a patient are imaged side by side, and the colors of the subject and the color reference in the captured color image are compared, thereby estimating the color of the actual subject (see JP 4-367658 A). In dermatology, makeup counseling, or the like, the same color estimation method is also performed by photographing a color reference and a subject such as a skin surface of a patient or a counseled person side by side.

Moreover, in dentistry or the like, an imaging device which is pressed against the surface of an object, irradiates the object with light, and performs multi-wavelength spectroscopic measurement on the object (see WO 2004/36162), or the like is also used.

SUMMARY OF THE INVENTION

Meanwhile, in the method using a number of a specified color tone of the shade guide, there is a problem in that it is not possible to eliminate a risk of causing deviation between a color tone of an artificial tooth or a dental prosthesis required by a dentist and a color tone of an artificial tooth or a dental prosthesis prepared by a dental technician.

In a color adjustment method of a dental prosthesis in the color management system (CMS) for dentistry disclosed in JP 4-367658 A or the like, a light source is specified, a color reference such as a shade guide provided with a reference color display portion and a subject such as a tooth of a patient are imaged side by side by a camera or an imaging element, and an actual color of the reference color of the color reference is compared with a color of the reference color of the color reference in a captured color image (photograph or monitor display). Accordingly, it is possible to match the color tone of the artificial tooth or the dental prosthesis with a color tone of the actual tooth of the patient. However, in the method, a dentist has to perform the imaging using a camera with one hand in a state of holding the color reference near the subject with the other hand, and hence, workability is extremely bad and the dentist cannot see a finder. Accordingly, there is a problem in that only a photograph with an inappropriate composition or lighting can be photographed.

Moreover, in an image processing system such as the CMS for dentistry disclosed in WO 2004/36162, multi-wavelength spectroscopic measurement can be performed on an object by using an imaging device. Accordingly, it is possible to reproduce a color to a high degree, and it is also possible to adjust a color tone to a high degree. However, there is a problem in that the imaging device or the processing device of the image processing system is an extremely expensive dedicated device, and thus, is not used in general photographing or the like and does not become widespread among the general public.

In contrast, in photographing a normal subject, a method of calibrating a normal digital camera of three colors of RGB with a color chart or the like is known. In this case, by creating a table accurately, it is possible to make a color difference $\Delta E$ equal to or less than 2. Since such accuracy is sufficient for preparing an artificial tooth or a dental prosthesis for dental implant or the like, an inexpensive measurement system capable of using a general-purpose digital camera has been expected.

However, in dentistry or the like, when photographing a stereoscopic object such as an artificial tooth or a prosthesis using a color reference such as a shade guide, and performing color tone adjustment, high-accuracy color tone adjustment is required. Accordingly, there is a problem in that a normal digital camera of three colors of RGB for photographing a normal subject has not been used.

A first object of the invention is to solve the above-described problems in the prior art and to provide a camera system, a dental camera system, a skin measuring camera system, a color conversion device, a color conversion method, and a computer-readable recording memory or medium in which is stored a color conversion program capable of performing simple photographing by a general-purpose digital camera of three colors of RGB without using an expensive dedicated imaging device, and besides, capable of accurately converting image data, that is obtained by photographing a stereoscopic subject composed of a stereoscopic object according to an illumination condition, such as an illumination geometric condition or an illumination light quality condition, to colorimetric values (colorimetric image data), and outputting the colorimetric values.

In addition to the first object, a second object of the invention is to provide a camera system, a dental camera system, a skin measuring camera system, a color conversion device, a color conversion method, and a computer-readable recording memory or medium in which is stored a color conversion program capable of outputting a gloss feeling of the photographed stereoscopic subject along with the colorimetric values (colorimetric image data) of the image data thereof.

In addition to the first and second objects, a third object of the invention is to provide a camera system, a dental camera system, a skin measuring camera system, a color conversion device, a color conversion method, and a computer-readable recording memory or medium in which is stored a color conversion program capable of accurately reproducing a color of a minute stereoscopic structure such as a texture of a surface of the photographed stereoscopic subject, as well as a color of an entire stereoscopic structure thereof, and obtaining a feeling of unevenness of the surface.

In order to solve the above-described problems, the present inventors conducted intensive examination. In order to clarify the above-described problems, as an example, by the method of calibrating a digital camera of three colors of RGB with a color chart or the like, a stereoscopic object was photographed by a digital camera (DSC) and a color image thereof was subjected to colorimetric conversion with a conversion table which was accurately created using a color chart. As a result, it was found that the color of the stereoscopic object has a value significantly different from a value obtained by a reference measuring instrument. Then, in order to improve the accuracy of the colorimetric conversion, measures such as increase of the number of patches of the color chart and the like were taken, and the above-described method was attempted again. However, it was found that an improved result is not obtained. Therefore, it was estimated that variation in an amount of light affects the deviation of color, and a white plate was used to control the amount of light. However, it was found that the amount of light is not necessarily stabilized. That is, it was found that, in the above-described method, even if the color chart or the like can perform color measurement with high accuracy, sufficient accuracy is not obtained with respect to a color measurement of a stereoscopic object. As the results of the above, it was found that, in close-photographing of a stereoscopic object, if illumination conditions such as illumination geometric conditions including at least a measurement angle with respect to the stereoscopic object, and illumination light quality conditions are considered, a color image of the subject such as a tooth of a patient, skin, hide, or a celom inner wall of human which is photographed using an inexpensive general-purpose digital camera can be colorimetrically converted with high accuracy, and thus, the present invention was accomplished.

That is, a camera system according to a first aspect of the present invention comprises a photographing unit which photographs a stereoscopic subject to acquire first image data; a database which stores a plurality of stereoscopic color profiles, in which a plurality of conversion relationships calculated from second image data obtained by photographing a plurality of reference color stereoscopic objects assigned with reference colorimetric values in advance by the photographing unit and the reference colorimetric values corresponding to the second image data are associated with a plurality of illumination conditions including illumination geometric conditions in the photographing of the reference color stereoscopic objects; a selection unit which, based on an illumination condition at the time of photographing of the stereoscopic subject, selects a stereoscopic color profile corresponding to the illumination condition from among the plurality of stereoscopic color profiles stored in the database; and a color conversion unit which performs color conversion from the first image data of a photographed image of the stereoscopic subject photographed by the photographing unit to colorimetric values (colorimetric image data), based on the stereoscopic color profile selected by the selection unit.

Herein, it is preferable that the plurality of reference color stereoscopic objects are reference color stereoscopic objects of three or more colors, and the plurality of stereoscopic color profiles are respectively created according to the plurality of illumination conditions for the respective reference color stereoscopic objects of three or more colors.

A camera system according to a second aspect of the present invention comprises a photographing unit which photographs a stereoscopic subject to acquire first image data; a database which stores a plurality of stereoscopic color correction profiles, in which a plurality of illumination conditions including illumination geometric conditions at the time of photographing by the photographing unit are associated with reference color stereoscopic objects assigned with reference colorimetric values in advance of one or more colors of similar colors of the stereoscopic subject; a selection unit which selects a corresponding stereoscopic color correction profile from among the plurality of stereoscopic color correction profiles stored in the database, based on an illumination condition at the time of photographing of the stereoscopic subject; and a color conversion unit which performs color conversion from the first image data of a photographed image of the stereoscopic subject photographed by the photographing unit to colorimetric values (colorimetric image data), based on a conversion relationship calculated from second image data obtained by photographing a plurality of planar color charts assigned with reference colorimetric values in advance and the reference colorimetric values, and the stereoscopic color correction profile selected by the selection unit.

Herein, in the camera system of the second aspect, it is preferable that the reference color stereoscopic objects of one or more colors is a reference color stereoscopic object of one color of the similar color of the stereoscopic subject, the plurality of stereoscopic color correction profiles are respectively created according to the plurality of illumination conditions for the reference color stereoscopic object of one color, and the plurality of planar color charts are planar color charts of three or more colors.

It is preferable that the conversion relationship is a planar color profile, and the color conversion unit performs color conversion of the first image data of the photographed image to intermediate colorimetric values (intermediate colorimetric image data) of the photographed image using the planar color profile, and performs color correction of the intermediate colorimetric values of the photographed image color-converted using the selected stereoscopic color correction profile to create the colorimetric values of the photographed image.

Alternatively, it is preferable that the conversion relationship is a planar color profile, and the color conversion unit creates a stereoscopic color profile using the planar color profile and the selected stereoscopic color correction profile, and performs color conversion from the first image data of the photographed image of the stereoscopic subject to the colorimetric values of the photographed image based on the created stereoscopic color profile.

In the camera systems of the first and second aspects, it is preferable that the reference color stereoscopic objects have at least one of a curved surface, a stereoscopic shape, an uneven surface shape, and a layer structure which are identical or analogous to those of the stereoscopic subject, and are stereoscopic objects made of a material analogous to the stereoscopic subject.

It is preferable that the reference color stereoscopic objects include reference color stereoscopic objects having at least one of semi-transparency, non-transparency, a light scattering property, and a color tint of milky white and/or flesh color which are analogous to those of the stereoscopic subject.

It is preferable that the photographing unit includes a digital camera, and an illumination geometric condition includes geometric positional information of three of a light source, the digital camera, and the stereoscopic subject or the reference color stereoscopic objects.

It is preferable that the illumination geometric condition is at least one of an illumination angle and an illumination distance of the light source with respect to the stereoscopic subject or the reference color stereoscopic objects.

In the camera systems of the first and second aspects, it is preferable that the camera systems further include a condition determination unit which determines the illumination condition at the time of photographing of the stereoscopic subject, and the selection unit selects a stereoscopic color profile or a stereoscopic color correction profile corresponding to the illumination condition from the database, based on the illumination condition determined by the condition determination unit.

It is preferable that the illumination condition further includes an illumination light quality condition of illumination light at the time of photographing, in addition to the illumination geometric condition, and the condition determination unit determines the illumination geometric condition and the illumination light quality condition as the illumination condition.

It is preferable that the condition determination unit includes at least one of an incidental information acquisition unit which acquires incidental information at the time of photographing of the stereoscopic subject from the photographing unit, an image analysis unit which performs image analysis of the photographed image of the stereoscopic subject, and a condition list reference unit which is provided with a determination condition combination list set in advance, and determines the illumination condition from at least one of the incidental information acquired by the incidental information acquisition unit, an analysis result by the image analysis unit, and a selection result in the determination condition combination list of the condition list reference unit.

In the camera systems of the first and second aspects, it is preferable that the camera systems further include a gloss determination unit which determines gloss feeling of the stereoscopic subject, based on the colorimetric values (colorimetric image data) of the photographed image of the stereoscopic subject color-converted by the color conversion unit.

It is preferable that the gloss determination unit determines gloss feeling based on lightness obtained from the colorimetric values of the photographed image of the stereoscopic subject and clarity of a reflected image of a light source imaged on the stereoscopic subject.

A dental camera system according to a third aspect of the present invention comprises the camera system of the first or second aspect, in which the stereoscopic subject is a human tooth, and the reference color stereoscopic objects have semi-transparency, a light scattering property, and a color tint of milky white which are analogous to those of the human tooth.

A skin measuring camera system according to a fourth aspect of the present invention comprises the camera system of the first or second aspect, in which the stereoscopic subject is human skin (hide), and the reference color stereoscopic objects have at least one of semi-transparency or non-transparency, a light scattering property, and a color tint of milky white or flesh color which are analogous to those of the human skin (hide).

A color conversion device according to a fifth aspect of the present invention comprises a database which stores a plurality of stereoscopic color profiles, in which a plurality of conversion relationships calculated from second image data obtained by photographing a plurality of reference color stereoscopic objects assigned with reference colorimetric values in advance and the reference colorimetric values corresponding to the second image data are associated with a plurality of illumination conditions including illumination geometric conditions in the photographing of the reference color stereoscopic objects; a selection unit which, based on an illumination condition at the time of photographing of the stereoscopic subject, selects a stereoscopic color profile corresponding to the illumination condition from among the plurality of stereoscopic color profiles stored in the database; and a color conversion unit which performs color conversion from first image data of a photographed image of the stereoscopic subject to colorimetric values (colorimetric image data), based on the stereoscopic color profile selected by the selection unit.

A color conversion device according to a sixth aspect of the present invention comprises a database which stores a plurality of stereoscopic color correction profiles, in which a plurality of illumination conditions including illumination geometric conditions at the time of photographing are associated with reference color stereoscopic objects assigned with reference colorimetric values in advance of one or more colors of similar colors of the stereoscopic subject; a selection unit which selects a corresponding stereoscopic color correction profile from among the plurality of stereoscopic color correction profiles stored in the database based on an illumination condition at the time of photographing of the stereoscopic subject; and a color conversion unit which performs color conversion from first image data of a photographed image of the stereoscopic subject to colorimetric values (colorimetric image data), based on a conversion relationship calculated from second image data obtained by photographing a plurality of planar color charts assigned with reference colorimetric values in advance and the reference colorimetric values, and the stereoscopic color correction profile selected by the selection unit.

A color conversion method according to a seventh aspect of the present invention comprises creating a database which stores a plurality of stereoscopic color profiles, in which a plurality of conversion relationships calculated from second image data obtained by photographing a plurality of reference color stereoscopic objects assigned with reference colorimetric values in advance and the reference colorimetric values corresponding to the second image data are associated with a plurality of illumination conditions including illumination geometric conditions in the photographing of the reference color stereoscopic objects; photographing a stereoscopic subject to acquire first image data; based on an illumination condition at the time of photographing of the stereoscopic subject, selecting a stereoscopic color profile corresponding to the illumination condition from among the plurality of stereoscopic color profiles stored in the database; and performing color conversion from the first image data of a photographed image of the stereoscopic subject to colorimetric values (colorimetric image data), based on the selected stereoscopic color profile.

A color conversion method according to an eighth aspect of the present invention comprises creating a database which stores a plurality of stereoscopic color correction profiles, in which a plurality of illumination conditions including illumination geometric conditions at the time of photographing are associated with reference color stereoscopic objects assigned with reference colorimetric values in advance of one or more colors of similar colors of the stereoscopic subject; photographing the stereoscopic subject to acquire first image data; selecting a corresponding stereoscopic color correction profile from among the plurality of stereoscopic color correction profiles stored in the database, based on an illumination condition at the time of photographing of the stereoscopic subject; and performing color conversion from the first image data of a photographed image of the stereoscopic subject to colorimetric values (colorimetric image data), based on a conversion relationship calculated from second image data obtained by photographing a plurality of planar color charts assigned with reference colorimetric values in advance and the reference colorimetric values, and the selected stereoscopic color correction profile.

A computer-readable recording memory or medium in which is stored a color conversion program according to a ninth aspect of the present invention is a computer-readable recording memory or a computer-readable recording medium in which is stored a color conversion program which causes a computer to execute the respective procedures of the color conversion method of the seventh or eighth aspect, or a color conversion program which causes a computer to execute the respective steps of the color conversion method of the seventh or eighth aspect.

According to the respective aspects of the invention, with the respective configurations described above, it is possible to perform simple photographing by a general-purpose digital camera of three colors of RGB and the like, without using an expensive dedicated imaging device, and it is also possible to accurately convert image data obtained by photographing a stereoscopic subject composed of a stereoscopic object to colorimetric values by using a stereoscopic color profile or a stereoscopic color correction profile and a planar color profile created in advance using a reference color stereoscopic object and selected according to an illumination condition such as an illumination geometric condition or an illumination light quality condition, and to output the colorimetric values.

Moreover, according to the respective aspects of the invention, with the respective configurations described above, in addition to the above-described effects, it is possible to obtain feeling of unevenness with improved color reproduction of a minute stereoscopic structure of a detail such as a texture of a surface of the photographed stereoscopic subject, and it is also possible to obtain gloss feeling of the photographed stereoscopic subject.

Figure 1:
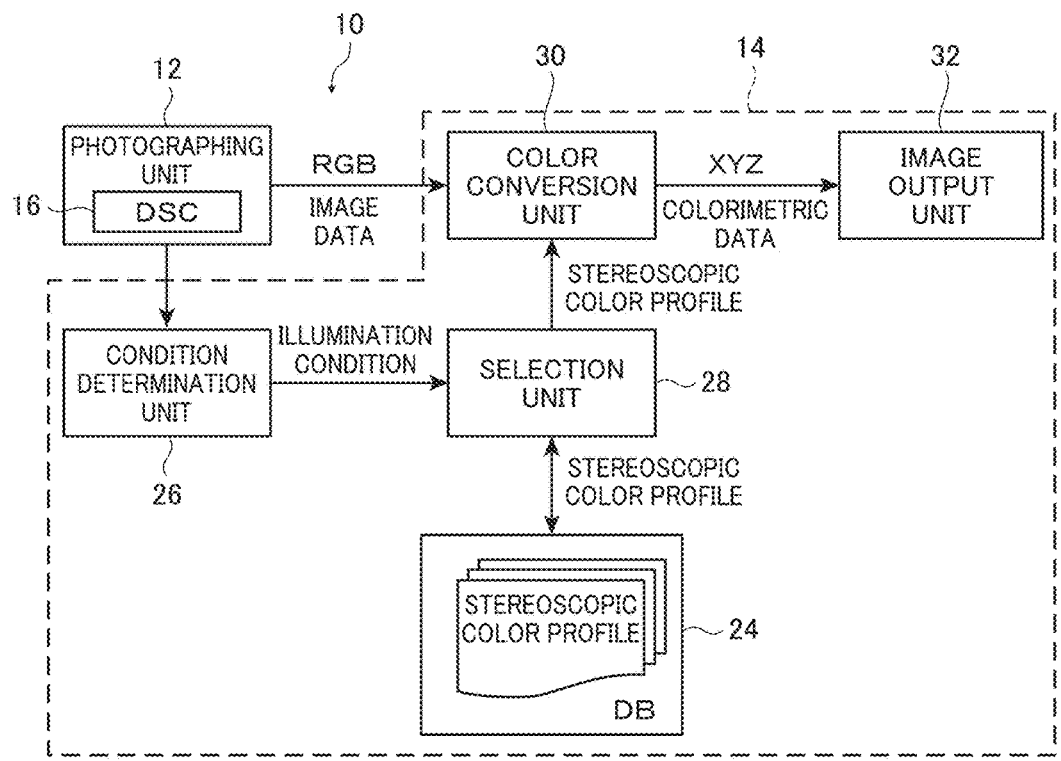
FIG. 1 is a block diagram schematically showing an example of the configuration of a camera system using a color conversion device according to a first embodiment of the present invention.

Each of FIGS. 4A, 4B, 4C, and 4D is a block diagram schematically showing an example of the configuration of a condition determination unit in the color conversion device of the camera system shown in FIG. 1.

Figure 5:
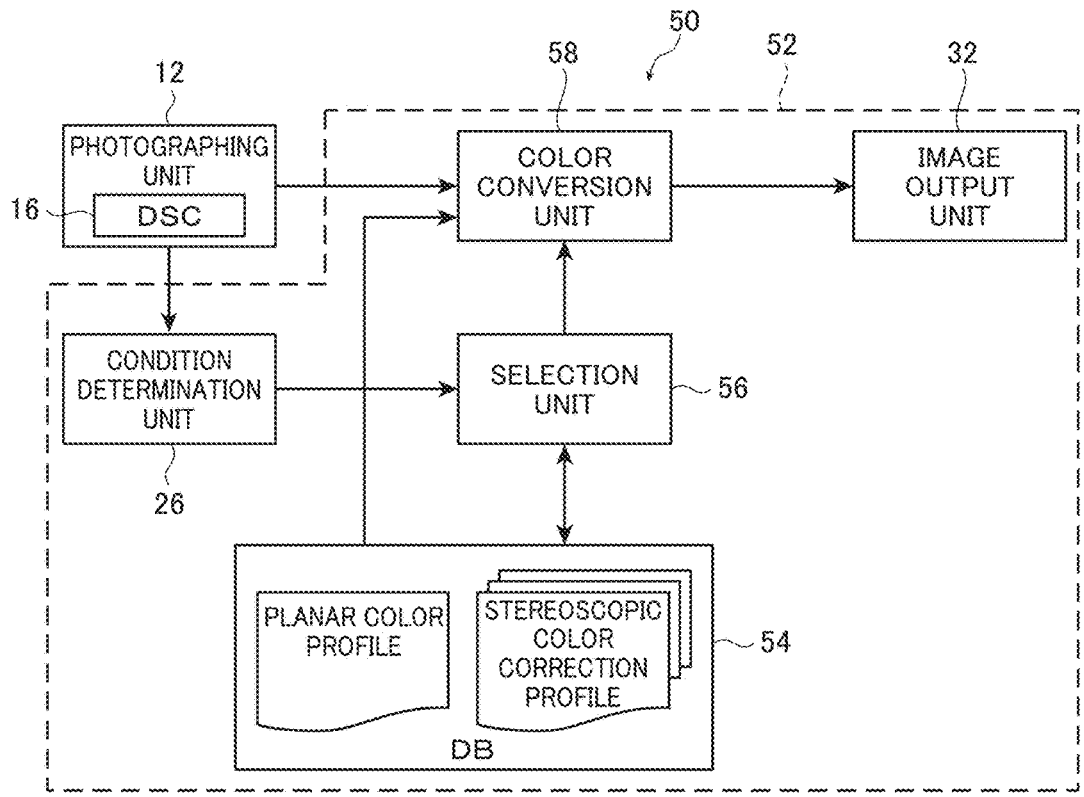

FIG. 5 is a block diagram schematically showing an example of the configuration of a camera system using a color conversion device according to a second embodiment of the present invention.

Figure 6:
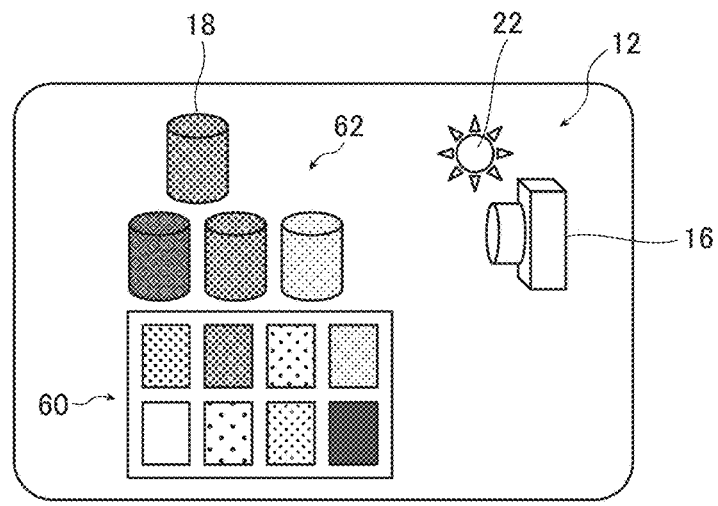

FIG. 6 is a schematic view schematically showing an example of a photographing unit of the camera system shown in FIG. 5, a stereoscopic subject to be photographed, a planar color chart, and a reference color stereoscopic object.

Figure 7A:
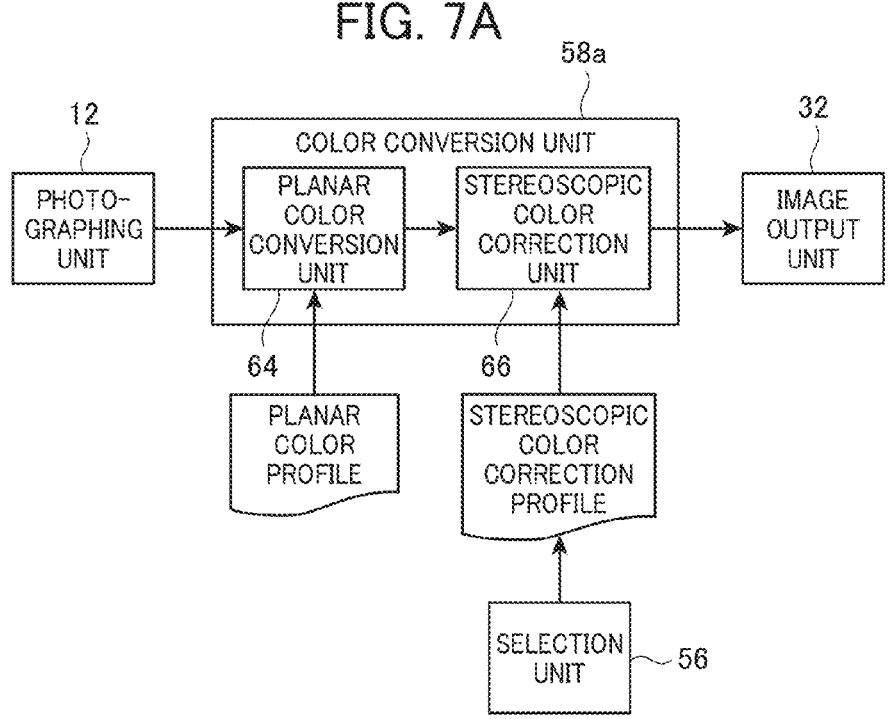
Figure 7B:
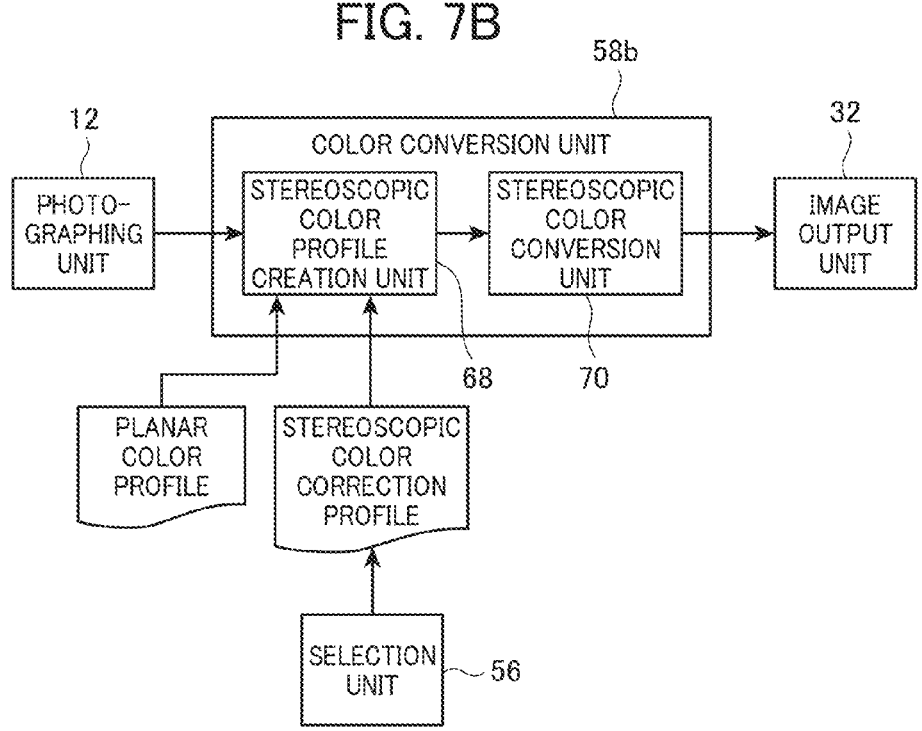

Each of FIGS. 7A and 7B is a schematic block diagram illustrating a color conversion unit of the camera system shown in FIG. 5.

FIG. 8 is a block diagram schematically showing an example of the configuration of a camera system using a color conversion device according to a third embodiment of the present invention.

Figure 9:
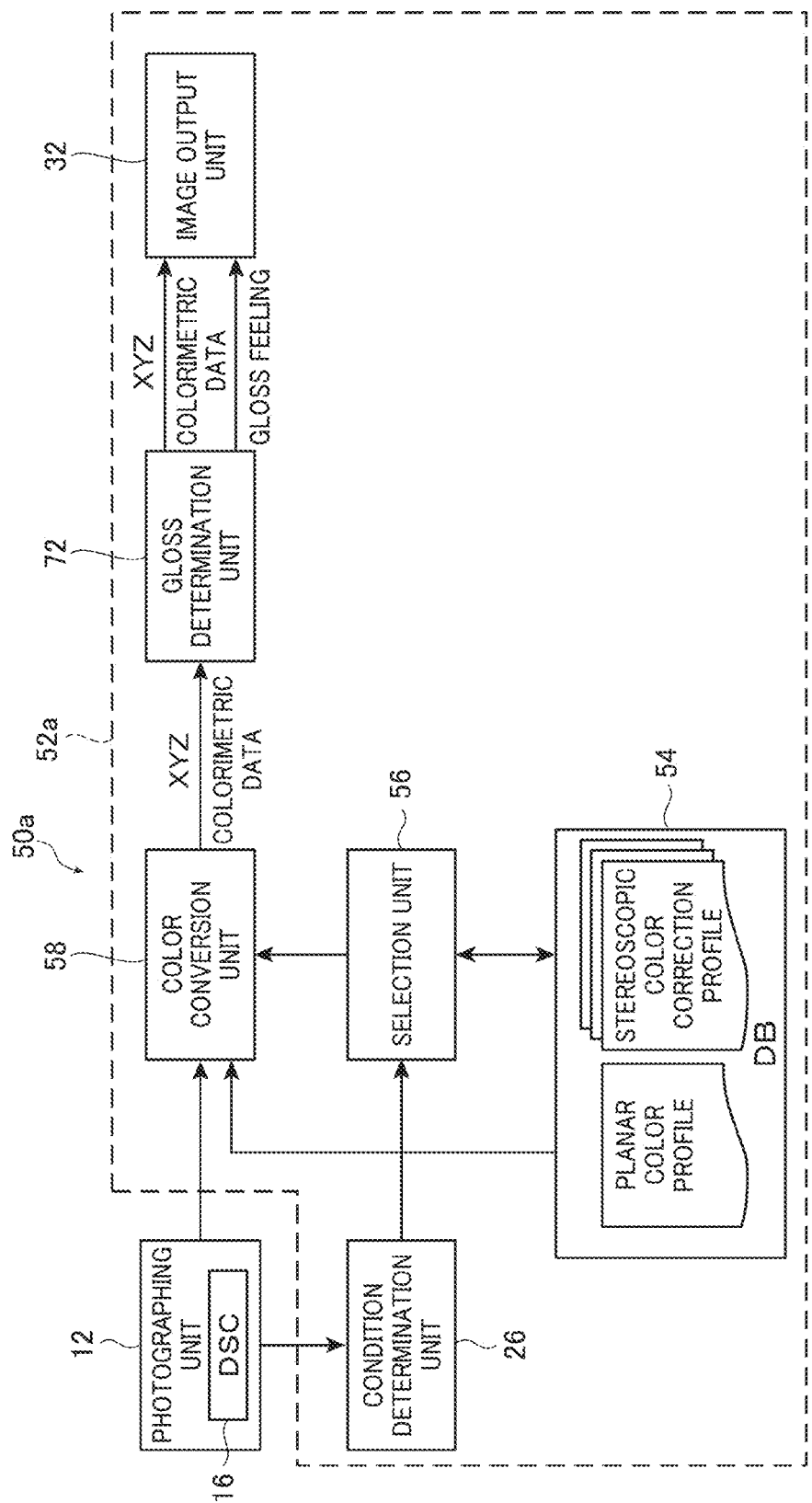

FIG. 9 is a block diagram schematically showing an example of the configuration of a camera system using a color conversion device according to a fourth embodiment of the present invention.

Each of FIGS. 10A and 10B is a schematic view showing a stereoscopic subject after ternarization having different reflected image clarity to be determined by a gloss determination unit in the color conversion device of the camera system shown in FIG. 8.

FIGS. 11A and 11B are respectively a plan view and a side view schematically showing an example of an oval (semioval) reference color stereoscopic object used in the present invention, and FIG. 11C is a plan view schematically showing an example of a polyhedral reference color stereoscopic object used in the present invention.

FIG. 12 is a graph showing the relationship between reflected light intensity and an inclination angle of a surface of a reference color stereoscopic object having an inclined surface photographed by a camera and used in the present invention.

FIGS. 13A and 13B are schematic views respectively showing a stereoscopic subject having specular reflection regions, and an analysis region and a non-analysis region of a photographed image of the stereoscopic subject.

DETAILED DESCRIPTION OF THE INVENTION

Hereinafter, a camera system, a dental camera system, a skin measuring camera system, a color conversion device, a color conversion method, a color conversion program, and a storage medium according to the present invention will be described in detail referring to exemplary embodiments shown in the accompanying drawings.

Figure 2:
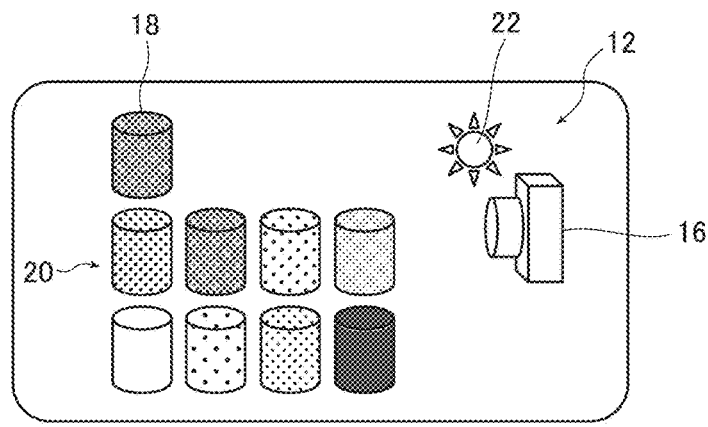
FIG. 2 is a schematic view schematically showing an example of a photographing unit of the camera system shown in FIG. 1, a stereoscopic subject to be photographed, and a reference color stereoscopic object.

FIG. 1 is a block diagram schematically showing an example of the configuration of a camera system using a color conversion device according to a first embodiment of the present invention. FIG. 2 is a schematic view schematically showing an example of a photographing unit of the camera system shown in FIG. 1, a stereoscopic subject to be photographed, and a reference color stereoscopic object.

In the following description, first, in regard to a specific example of the camera system according to the present invention, a dental camera system in a CMS for dentistry will be primarily described as a representative example. However, the present invention is not limited to a dental camera system, and needless to say, may be applied to various camera systems such as a skin measuring (diagnostic) camera system and an endoscope camera system.

As shown in FIG. 1, the camera system 10 has a photographing unit 12 which photographs a stereoscopic subject to acquire image data of three colors, and a color conversion device 14 which color-converts the image data acquired by the photographing unit 12 to colorimetric values (colorimetric image data).

As shown in FIG. 2, the photographing unit 12 includes a digital camera (digital still camera: DSC) 16, and a photographing light source 22 which irradiates a subject, such as a stereoscopic subject 18 or a plurality of stereoscopic references (also referred to as stereoscopic charts) 20 as a reference color stereoscopic object, with illumination light at the time of photographing by the digital camera 16.

As the digital camera 16, a general-purpose digital camera which photographs a subject to acquire image data of three colors of RGB can be used. The digital camera 16 photographs a subject such as a stereoscopic subject 18 to acquire image data of three colors, for example, image data of RGB (hereinafter, represented by RGB image data) and stores the image data in an internal image memory (not shown) or the like as an image file. Preferably, when a flash is provided, information regarding the on and off of the flash, focusing information on a subject such as a stereoscopic subject 18, or the like can be stored in the image memory as incidental information of the image file, that is, tag information. The tag information, which will be described below, is transmitted to a condition determination unit 26 of the post-stage color conversion device 14.

The digital camera 16 is not limited to a digital still camera, and may be a digital video camera. In the present invention, although an inexpensive general-purpose digital camera can also be used, the digital camera 16 is not particularly limited, and any digital camera may be used. Image data acquired by the digital camera 16 is not limited to RGB image data, and device-dependent data such as CMY image data, YIQ image data, sRGB image data, or the like can also be used.

The photographing light source (hereinafter, simply also referred to as light source) 22 emits illumination light at the time of photographing of a subject such as a stereoscopic subject 18 or a stereoscopic reference 20 with the digital camera 16. Any light source may be used as long as a subject can be illuminated such that the subject can be appropriately photographed with the digital camera 16, and examples of the light source include a ring light flash for shadowless photographing provided over the entire circumference of a lens of the digital camera 16, an illumination device for dentistry and a ring light for dentistry used at the time of treatment of a human tooth, a room lamp (fluorescent lamp or the like), and the like. As the ring light flash or the ring light, a ring light flash or a ring light used for shadowless photographing can be used.

A photographing subject of the camera system 10 of the present invention is a stereoscopic subject 18 composed of a stereoscopic object schematically shown in FIG. 2. The stereoscopic subject 18 can be, but not limited to, a human tooth, human skin (hide), a human celom inner wall such as a human esophagus inner wall, or the like.

The stereoscopic subject 18 has a predetermined curved surface, a stereoscopic shape, an uneven surface shape, and a layer structure, and is regarded as a stereoscopic structure such as a polyhedron composed of a plurality of flat surfaces or a curved surface, and in particular, a polyhedron composed of a surface having a predetermined angle. For example, a human tooth, human skin (hide), a human celom inner wall, or the like has a predetermined curved surface, a stereoscopic shape, an uneven surface shape, and a layer structure which are distinctive for each of them. In particular, a human tooth or the like has a two-layer structure composed of a semi-transparent surface layer and a white inner layer. Human skin, hide, or the like has a three-layer structure of a horny layer, an epidermis, and a corium and has an uneven surface shape recessed from the surface of the skin (hide), like wrinkles or pores, that is, a minute stereoscopic structure called a texture. Similarly, a human celom inner wall or the like has a multilayer structure, and has an uneven shape such as minute surface unevenness. The stereoscopic object can be approximated to a stereoscopic structure such as a polyhedron, including a minute stereoscopic structure or an uneven shape.

Accordingly, in the present invention, although a stereoscopic structure of a stereoscopic object as a whole is normally set as the stereoscopic subject 18, the invention is not limited thereto. For example, as described above, like human hide or skin, a human celom inner wall, or the like, when a stereoscopic object has a minute stereoscopic structure or an uneven shape called a texture in the surface thereof, the minute stereoscopic structure or the uneven shape of a part of the surface of the stereoscopic object or the detail of the stereoscopic object may be set as the stereoscopic subject 18, instead of the entire stereoscopic object, or in addition to the stereoscopic structure of the stereoscopic object as a whole, the minute stereoscopic structure or the uneven shape of the detail or the like of the stereoscopic object may be set as the stereoscopic subject 18, and in this case, the entire stereoscopic object may be approximated to a stereoscopic structure such as a polyhedron, including the minute stereoscopic structure or the uneven shape.

When both the stereoscopic structure of the stereoscopic object as a whole and the minute stereoscopic structure or the uneven shape of the detail or the like of the surface of the stereoscopic object are set as the stereoscopic subject 18, or when the stereoscopic object is approximated as a polyhedron structure including a minute structure, it is possible to achieve color reproduction with excellent accuracy for the minute stereoscopic structure or the uneven shape of the detail as well as the entire stereoscopic object.

The stereoscopic references 20 shown in FIG. 2 are subjects of the digital camera 16 of the photographing unit 12 upon creating a stereoscopic color profile described below. Each of the stereoscopic references 20 is a stereoscopic object (stereoscopic color reference) to which a reference colorimetric value is assigned in advance and which has a stereoscopic structure, such as a polyhedron having a curved surface or a polyhedron composed of a plurality of flat surfaces having an angle or a plurality of curved surfaces, and in particular, a polyhedron with flat surfaces having a predetermined angle, and is a reference color stereoscopic object of the present invention. In the present invention, although a plurality of different colors, and accordingly, a plurality of stereoscopic references 20 of different colors are used, preferably, three or more colors, that is, three or more stereoscopic references 20 of different colors are used. In the example shown in FIG. 2, eight stereoscopic references 20 are used.

As the stereoscopic references 20 when a minute stereoscopic structure of a detail is set as the stereoscopic subject 18, reference color stereoscopic objects depending on a minute stereoscopic structure, an uneven shape, or a stereoscopic structure such as a polyhedron including the minute stereoscopic structure or the uneven shape are preferably used.

A case where the stereoscopic subject 18 and the stereoscopic references 20 relate to a minute stereoscopic structure or an uneven shape of a detail will be described below.

The stereoscopic references 20 preferably have a curved surface identical or analogous to the curved surface of the stereoscopic subject 18, and in particular, have a gently changing curved surface or a plurality of flat surfaces having an angle. The stereoscopic references 20 are preferably stereoscopic objects having a stereoscopic shape identical or analogous to that of the stereoscopic subject 18, for example, a human tooth, human skin or hide, a human celom inner wall such as a human esophagus, or stereoscopic objects having a stereoscopic structure identical or analogous to that of the stereoscopic subject 18, such as a polyhedron. Also, the stereoscopic references 20 are preferably stereoscopic objects having an uneven surface shape identical or analogous to that of the stereoscopic subject 18.

For example, when the stereoscopic subject 18 is a human tooth, as the stereoscopic reference 20, an oval (semioval) stereoscopic reference (reference color stereoscopic object) 20a shown in FIG. 11A or 11B which is a stereoscopic object having a predetermined curved surface, or a polyhedral (for example, gem-like) stereoscopic reference (reference color stereoscopic object) 20b shown in FIG. 11C which is a stereoscopic object having predetermined inclined flat surfaces is preferably used. As described above, it is preferable to select the shape or structure of the stereoscopic object of the stereoscopic reference 20 depending on the stereoscopic subject 18.

More preferably, the stereoscopic references 20 may have at least one of semi-transparency, non-transparency, a light scattering property, and a color tint of milky white and/or flesh color which are analogous to those of the stereoscopic subject 18, such as a tooth, skin or hide, or a celom inner wall of human.

In the case of a human tooth, a tooth whose color falls within the following colorimetric values, for example, within the indexes of the following maximum value (Max)–minimum value (Min) in a three-dimensional color space of CIE Lab can be selected as a target of the stereoscopic references 20.

TABLE 1

| | CIE Lab D65 light source | | |
| --- | --- | --- | --- |
| | L | a | b |
| Representative Value | 71.8 | 1.0 | 17.8 |
| Max | 74 | 3 | 24 |
| Min | 61 | −1 | 12 |

In the case of a Japanese skin (hide), for example, flesh color can be defined by lightness of 5.5 to 7 and hue of 10R to 10YR in a Munsell color chart (Munsell color sample table: Munsell color system), and can be defined by lightness L* of 60 to 80 and chromaticity indexes a* of 10 to 20 and b* of 5 to 30 in a CIE Lab color system (L*a*b* color system).

More preferably, the stereoscopic references 20 have a layer structure analogous or identical to the stereoscopic subject 18, such as a tooth, hide or skin, or a celom inner wall of human. For example, the stereoscopic references 20 more preferably have a two-layer structure of a semi-transparent surface layer and a white inner layer in the case of a human tooth or the like, and more preferably have a three-layer structure of a horny layer, an epidermis, and a corium in the case of human hide. However, in the present invention, the stereoscopic references 20 having a layer structure may include stereoscopic references having at least one layer among a plurality of layers constituting the layer structure of the stereoscopic subject 18. Still more preferably, the stereoscopic references 20 are made of a material identical or analogous to the stereoscopic subject 18, such as a tooth, hide, skin, or a celom inner wall of human. For example, still more preferably, the stereoscopic references 20 are made of a material such as enamel or dentin, in the case of a human tooth or the like, and are prepared by coloring a base material such as silicon or urethane with a dye, a pigment or the like, in the case of hide or skin, or a celom inner wall of human.

As described above, the stereoscopic references 20 are preferably composed of stereoscopic objects having at least one of a curved surface, a stereoscopic shape, an uneven surface shape, a layer structure, and a stereoscopic structure such as a polyhedron composed of a plurality of flat surfaces or a plurality of curved surfaces, and in particular, a polyhedron with surfaces having a predetermined angle, which are identical or analogous to those of the stereoscopic subject 18, and are made of a material analogous to the stereoscopic subject 18.

In the present invention, it is preferable that the stereoscopic subject 18 which is a principal subject is photographed along with one or more stereoscopic references 20.

The color conversion device 14 includes a database (DB) 24 which stores a plurality of stereoscopic color profiles representing the conversion relationship between reference colorimetric values obtained according to a plurality of illumination conditions for the plurality of stereoscopic references 20 in advance and image data of three colors of RGB of a photographed image of the digital camera 16, a condition determination unit 26 which determines an illumination condition for illuminating the stereoscopic subject 18 at the time of photographing by the photographing unit 12, a selection unit 28 which selects a corresponding stereoscopic color profile from the database 24 based on the illumination condition at the time of photographing of the stereoscopic subject 18, a color conversion unit 30 which color-converts RGB image data of the image of the stereoscopic subject 18 photographed by the photographing unit 12 to colorimetric values (for example, XYZ colorimetric values) based on the stereoscopic color profile selected by the selection unit 28, and an image output unit 32 which outputs a colorimetric image (for example, an XYZ colorimetric image) of the stereoscopic subject 18 color-converted by the color conversion unit 30.

The database 24 stores the stereoscopic color profiles in which the correspondence between RGB image data of three colors of a photographed image obtained by photographing one stereoscopic reference 20 assigned with a reference colorimetric value in advance under a predetermined illumination condition including a predetermined illumination geometric condition by the digital camera 16 of the photographing unit 12 and the reference colorimetric value of the stereoscopic reference 20, that is a conversion relationship, and a predetermined illumination condition at the time of photographing are associated with a plurality of stereoscopic references 20 assigned with reference colorimetric values in advance. The database 24 stores a plurality of stereoscopic color profiles, in which the conversion relationship between RGB image data photographed for each of a plurality of different illumination conditions and the reference colorimetric value and a plurality of illumination conditions at the time of photographing are associated with one stereoscopic reference 20, for each of a plurality of illumination conditions. Further, the database 24 stores a plurality of sets of stereoscopic color profiles corresponding to the plurality of stereoscopic references 20, since a set of a plurality of stereoscopic color profiles for each of a plurality of illumination conditions by one stereoscopic reference 20 is obtained for each of the plurality of stereoscopic references 20.

The stereoscopic color profile stored in the database 24 is used for colorimetric conversion of RGB image data of three colors of a photographed image to colorimetric values (colorimetric image data). The stereoscopic color profile is not particularly limited, and a three-dimensional look-up table (3D LUT), a three-dimensional matrix, or the like for conversion between RGB image data and the colorimetric values is preferably used. A colorimetric conversion relational expression between RGB image data and the colorimetric values may be used. Any means may be used as long as colorimetric conversion between RGB image data and the colorimetric values is possible. A known 3D LUT, three-dimensional matrix, colorimetric conversion relational expression, or the like for colorimetric conversion from RGB image data to the colorimetric values (colorimetric image data) can be used.

In the present invention, although the illumination conditions associated with the conversion relationship between the colorimetric values and RGB image data in the stereoscopic color profile should include at least illumination geometric conditions, the illumination conditions preferably include illumination light quality conditions in addition to the illumination geometric conditions. More preferably, when there is external light, ambient light, or the like in addition to illumination light for photographing, as the illumination conditions, it is preferable to consider an external environmental condition, such as external light, indoor light, or ambient light from an indoor lamp (room lamp) such as a fluorescent lamp, an illumination device for dentistry, or the like. When a light source exclusively for photographing such as an illumination flash for photographing is not turned on, external light or ambient light becomes illumination light for photographing. Accordingly, an indoor lamp such as a fluorescent lamp, an illumination device for dentistry, or the like can be handled as the light source 22.

In the present invention, illumination geometric conditions as the illumination conditions need to include at least an illumination angle of the stereoscopic subject 18 by the light source 22. Preferably, the illumination geometric conditions include the illumination angle and an illumination distance of the stereoscopic subject 18 by the light source 22. The illumination angle refers to an angle between the light source 22 and the digital camera 16 when viewed centering on the stereoscopic subject 18. The illumination distance can be set as the distance between the stereoscopic subject 18 and the light source 22.

As such illumination geometric conditions, or as geometric arrangement conditions for obtaining the illumination geometric conditions, geometric positional information of the light source, the subject, and the camera at the time of photographing of the subject, that is, geometric positional information representing a geometric arrangement relationship for determining the geometric positional relationship of the light source 22, the stereoscopic subject 18, and the digital camera 16, for example, when photographing the stereoscopic subject 18 illuminated by the light source 22 using the photographing unit 12 can be used. The geometric positional information can be transmitted to the condition determination unit 26 at the post stage of the photographing unit 12 as tag information of an image file of the digital camera 16. The geometric positions of the light source 22, the stereoscopic subject 18, and the digital camera 16 are determined by a combination of the positional relationships of (a) the light source 22 and the stereoscopic subject 18, (b) the stereoscopic subject 18 and the digital camera 16, and (c) the digital camera 16 and the light source 22.

Though details will be described below, when the digital camera 16 is provided with a flash, the flash becomes the light source 22. Accordingly, the positional relationship (c) between the digital camera 16 and the light source 22 is fixed and known. Then, if information regarding the distance between the digital camera 16 and the stereoscopic subject 18 of the positional relationship (b) is acquired, when the flash is on at the time of photographing, the positional relationship (a) can be obtained from the positional relationships (b) and (c). Information regarding the distance between the digital camera 16 and the stereoscopic subject 18 of the positional relationship (b), that is, a photographing distance can be obtained from, for example, focusing information of the stereoscopic subject 18 which is one kind of geometric positional information, or the like. When not only the focusing information to be acquired by the digital camera 16 but also information regarding the photographing distance is acquired, the information regarding the photographing distance can be transmitted to the condition determination unit 26 at the post stage of the photographing unit 12 as tag information of an image file of the digital camera 16.

When the digital camera 16 is not provided with a light source exclusively for photographing such as an illumination flash for photographing, or while the digital camera 16 is provided with a light source exclusively for photographing such as a flash, when the flash is off, as described above, external light, indoor light, or ambient light from an indoor lamp (room lamp) such as a fluorescent lamp, an illumination device for dentistry, or the like becomes illumination light for photographing. For this reason, while the indoor lamp such as the fluorescent lamp, the illumination device for dentistry, or the like becomes the light source 22, the position thereof is fixed. Accordingly, if the position of the stereoscopic subject 18 at the time of photographing is determined, the position of the light source 22 is determined and the positional relationship (a) is determined, and as described above, if information regarding the distance between the digital camera 16 and the stereoscopic subject 18 of the positional relationship (b) is acquired, the positional relationship (c) can be determined.

From above, by using the tag information of the digital camera 16 such as the on/off information of the flash and the focusing information of the stereoscopic subject 18, the positional relationships (a), (b), and (c) can be determined.

In this way, if the positional relationships (a), (b), and (c) are determined, as the illumination geometric conditions, the illumination angle of the stereoscopic subject 18 by the light source 22, and further, the illumination distance can be obtained.

When determining such illumination geometric conditions, the on/off information of the flash and the focusing information of the stereoscopic subject 18 are transmitted as the tag information from the digital camera 16 to the post-stage condition determination unit 26, or the geometric positional information for determining the geometric positional relationship of the light source, the subject, and the camera, or information regarding the distance between the camera and the subject is acquired from the on/off information and the focusing information, and the acquired information is transmitted to the post-stage condition determination unit 26. Then, the condition determination unit 26 can acquire such information and can determine the illumination geometric conditions.

The condition determination unit 26 is preferably configured to acquire information regarding the geometric positions, other than the on/off information of the flash and the focusing information of the stereoscopic subject 18 acquired by the digital camera 16 as the tag information and transmitted to the condition determination unit 26, from information stored in a memory outside or inside of the condition determination unit 26, external input information, or the like.

Next, as the illumination light quality conditions as the illumination conditions, the light source characteristic of the light source 22, for example, at least one light quality information of a light scattering property, a polarization property, a spectral distribution, a color temperature, and the like of the light source 22 can be exemplified, and the light quality information can be transmitted to the post-stage condition determination unit 26. As one of the light quality information, the on/off information of the flash as the light source 22 can be used.

The condition determination unit 26 is preferably configured to acquire the light quality information, for example, information regarding the light source characteristic (illumination light quality) of the flash as the light source 22 when the flash is on or information regarding the light source characteristic (illumination light quality) of indoor light or illumination light of an illumination device for dentistry when the flash is off, from information stored in the memory outside or inside the condition determination unit 26, external input information, or the like.

As the external environmental condition as the illumination conditions, when the flash is on, the geometric position of an indoor lamp (room lamp) such as a fluorescent lamp or an illumination device for dentistry which emits external light, indoor light, ambient light, or the like, or the light source characteristic (light quality) of external light, indoor light, ambient light, or the like can be exemplified, and when the flash is not provided or is off and when illumination light for photographing or the like from the illumination device for dentistry or the like is irradiated, the geometric position of an indoor lamp (room lamp) such as a fluorescent lamp, or the light source characteristic (light quality) of external light, indoor light, ambient light, or the like can be exemplified.

The condition determination unit 26 is preferably configured to acquire the geometric position of a light source, such as external light, indoor light, ambient light or the like, or the light source characteristic (light quality) of external light, indoor light, ambient light, or the like from information stored in the memory outside or inside the condition determination unit 26, external input information, or the like.

The stereoscopic color profile associated with the above-described illumination conditions, and in particular, the illumination geometric conditions are created in the following manner and stored in the database 24. Herein, a case where the illumination angle, the on and off of the flash, and the photographing distance of the illumination geometric conditions are used as the illumination conditions at the time of creating the stereoscopic color profile, and at least the illumination angle and the illumination distance of the illumination geometric conditions are used as the illumination conditions for the management items of the stereoscopic color profile stored in the database 24 will be described.

First, a stereoscopic reference 20 of a predetermined color assigned with a reference colorimetric value in advance is photographed by the digital camera 16 multiple times while changing the illumination angle, the on and off of the flash, and the photographing distance to acquire RGB image data of a photographed image of the stereoscopic reference 20 for a plurality of illumination angles. A stereoscopic color profile, in which a conversion relationship is established by causing the reference colorimetric value assigned to the stereoscopic reference 20 in advance to correspond the acquired RGB image data of the photographed image of the stereoscopic reference 20, is created according to each of a plurality of illumination angles, the on and off of the flash, and a plurality of photographing distances. Thus, a set of a plurality of stereoscopic color profiles for one stereoscopic reference 20 is created.

Subsequently, the stereoscopic reference 20 is changed to a stereoscopic reference 20 of a different color assigned with a different reference colorimetric value in advance, and similarly, a set of a plurality of stereoscopic color profiles for defining the conversion relationship between a different reference colorimetric value and measured RGB image data according to each of a plurality of illumination angles, the on and off of the flash, and a plurality of photographing distances is created. This is continued until all sets of a plurality of stereoscopic color profiles for the stereoscopic references 20 of a plurality of different colors, preferably three or more colors, prepared in advance are created.

Each set of all sets of a plurality of stereoscopic color profiles obtained as above is associated with a plurality of illumination angles and the all sets are stored in the database 24.

Although the conversion relationship between colorimetric values (reference colorimetric values) and an RGB signal value (RGB image data) of the digital camera 16 according to the illumination angle (measurement angle), the on and off of the flash, and the photographing distance (illumination distance) of the illumination geometric conditions is obtained for the stereoscopic references 20 of a plurality of colors, for example, three or more colors, and stereoscopic color profiles which are managed in the database 24 with the illumination angle as a management item are created, the invention is not limited thereto, and both the illumination angle and the illumination distance (distance) of the illumination geometric conditions may be used as management items.

It is more preferable that the on and off condition of the flash is further added to the illumination angle and the illumination distance as the management items. Moreover, it is still more preferable that other light source characteristics, for example, the illumination light quality conditions are added to the above management items. Furthermore, it is still more preferable that colors suitable for the stereoscopic subject 18 are selected as the colors of the stereoscopic references 20.

Thus, the database 24 stores many stereoscopic color profiles, that is, a plurality of stereoscopic color profiles which represent the conversion relationship between the colorimetric values and RGB image data, and in which the management item is at least the illumination angle of the illumination geometric conditions as the illumination conditions.

In the database 24, for example, the illumination geometric conditions among the illumination conditions, and in particular, the illumination angle and the illumination distance can be managed in association with the stereoscopic color profile as management items. Hereinafter, as the "stereoscopic color profile" stored in the database 24, a "stereoscopic color profile" linked with management items of illumination conditions illustrated below, for example, the illumination geometric conditions of the illumination angle and the illumination distance, and further, illumination light quality conditions can be exemplified.

Example 1

Association of "stereoscopic color profile" linked with a combination of "illumination angle"×"illumination distance" as management items Example 2

Association of "stereoscopic color profile" linked with a combination of "illumination angle"×"illumination distance"×"light source characteristic (flash or the like)" as management items Herein, the "light source characteristic (flash or the like)" may be on and off of flash, other light source characteristics (directivity or the like), or photographing conditions.

Example 3

Association of "stereoscopic color (correction) profile" linked with "combination conditions" of management items of the respective illumination conditions Herein, it is assumed that a combination of management items of "illumination angle"×"illumination distance"× "light source characteristic or illumination light quality (flash or the like)" is fixed.

Examples of a database of "stereoscopic color (correction) profile" linked with "combination conditions" of the respective illumination conditions are shown in Table 2 and Table 3.

Combination A

TABLE 2

| Room A Fluorescent Lamp | Flash ON Distance 15 cm | Flash ON Distance 30 cm | Flash OFF Distance 15 cm | Flash OFF Distance 30 cm |
|---|---|---|---|---|
| Angle 0° | P1 | P4 | P7 | P10 |
| Angle 30° | P2 | P5 | P8 | P11 |
| Angle 45° | P3 | P6 | P9 | P12 |

Combination B

TABLE 3

| Room B Light Bulb Color | Flash ON Distance 15 cm | Flash ON Distance 30 cm | Flash OFF Distance 15 cm | Flash OFF Distance 30 cm |
|---|---|---|---|---|
| Angle 0° | P13 | P16 | P19 | P22 |
| Angle 30° | P14 | P17 | P20 | P23 |
| Angle 45° | P15 | P18 | P21 | P24 |

In the example shown in Combination A of Table 2, a room lamp of Room A is a fluorescent lamp, and when the flash is on (Flash ON), the photographing light source 22 becomes the flash, and the external environmental condition becomes indoor light from the fluorescent lamp. When the flash is off (Flash OFF), the photographing light source 22 is a fluorescent lamp, and light quality becomes a fluorescent lamp color. Thus, illumination light quality is changed.

In Table 2, stereoscopic color profiles P1 to P12 created for the combinations of management items of "illumination angle"×"illumination distance"×"illumination light quality (flash on and off)" are stored in the database 24 while changing the illumination distance from 15 cm to 30 cm and changing the illumination angle to 0°, 30°, and 45° when the flash is on and when the flash is off.

In the example shown in Combination B of Table 3, a room lamp of Room B is changed to a light bulb, for example, an incandescent bulb, and when the flash is on (Flash ON), the photographing light source 22 becomes the flash, and the external environmental condition becomes indoor light from the light bulb. When the flash is off (Flash OFF), the photographing light source 22 is the light bulb, light quality becomes a light bulb color, and illumination light quality is changed. The above points are different from Combination A shown in Table 2. However, the combinations of the illumination angle and the illumination distance are identical. Stereoscopic color profiles P13 to P24 created for the combinations of the management items of "illumination angle"×"illumination distance"×"illumination light quality (flash on and off)" are stored in the database 24.

In this way, the database 24 stores the stereoscopic color profiles according to various combinations of the management items of the illumination conditions.

The condition determination unit 26 determines the illumination conditions which include at least the illumination geometric conditions including the geometric arrangement conditions when illuminating the stereoscopic subject 18 at the time of photographing of the stereoscopic subject 18 by the photographing unit 12, for example, especially the illumination angle and the illumination distance representing the geometric arrangement of the photographing light source 22, the stereoscopic subject 18, and the digital camera 16. The illumination conditions determined by the condition determination unit 26, specifically, the illumination geometric conditions including the illumination angle and the illumination distance are used to select the stereoscopic color profiles stored in the database 24. Accordingly, it is necessary to determine the illumination conditions associated with the stereoscopic color profiles stored in the database 24. In other words, it is necessary to determine the illumination conditions which are the management items for managing the stereoscopic color profiles stored in the database 24.

In addition to the above-described illumination geometric conditions, the condition determination unit 26 preferably determines the illumination conditions including the illumination light quality conditions representing information, such as a light scattering property, a polarization property, a spectral distribution characteristic, a color temperature, and the like, defined by light quality of illumination light emitted from the photographing light source 22, for example, defined according to whether illumination light is a flash, and in particular, light of a ring light flash, whether illumination light is a special light of an illumination device for dentistry, a ring light for dentistry, or the like, and whether illumination light is light of a room lamp (fluorescent lamp or the like). In addition to the above-described illumination geometric conditions and the illumination light quality conditions, it is preferable to determine the illumination conditions including the external environmental condition of indoor light, external light, ambient light, or the like.

When the stereoscopic color profile is associated with the illumination conditions exemplified in the above Example 1) to Example 3) of the management items, the condition determination unit 26 determines the illumination conditions as follows.

In Example 1): The illumination angle and the illumination distance between the light source and the subject which are the illumination geometric conditions among the illumination conditions are determined.

In Example 2): In addition to Example 1), the illumination light quality conditions (the on and off of the flash and the like) among the illumination conditions are determined.

In Example 3): The positional relationship between the light source and the subject is determined, and the combination conditions of the management items are determined (see Table 2 and Table 3).

As described above, information regarding the respective management items (the illumination geometric conditions of the illumination angle, illumination distance, and the like, and the illumination light quality conditions (the on and off of the flash and the like)) of the illumination conditions of Example 1) to Example 3) can be acquired by various methods described below.

a) Information may be directly acquired from the incidental information (tag information) of the digital camera 16. For example, the photographing distance may be acquired from the focusing information.

b) Information may be estimated from the tag information of the digital camera 16.

c) The positional relationship among the light source 22, the stereoscopic subject 18, and the digital camera 16 may be calculated from the photographing distance of the digital camera 16 and the position of the light source 22.

d) Information may be acquired from the tag information of the digital camera 16 referring to any database (DB).

e) Information may be obtained from image analysis on the RGB image data of the photographed image of the digital camera 16.

f) Information may be estimated by comparing the size of the stereoscopic subject 18 in the image data of the photographed image with the size of the actual stereoscopic subject 18.

g) The position of the light source may be estimated from shadows generated in the curved surface or a plurality of flat surfaces of the stereoscopic reference 20 (reference color stereoscopic object).

For example, in the example of g) described above, when a stereoscopic reference 20 composed of a plurality of surfaces having different inclination angles, in particular, a stereoscopic reference 20 composed of a polyhedron is used, a brightly shining surface is analyzed from the photographed image of the stereoscopic reference 20, or the distribution of brightness Y, lightness L, or the like obtained from measurement of surface reflection of the stereoscopic reference 20, whereby it is possible to easily estimate the arrangement angle of the light source 22.

For example, in the case of photographing the stereoscopic reference 20 illuminated by the light source 22 by the digital camera 16, when the light source 22, the stereoscopic reference 20, and the digital camera 16 are in an optical geometric arrangement in which reflected light of the light source 22 reflected by a specific surface (a minute curved surface when a stereoscopic object composed of a curved surface is viewed discretely, or a flat surface of a polyhedron) of the stereoscopic reference 20 enters the photographing lens of the digital camera 16, if the inclination angle of the specific surface is 0°, reflected light of the light source 22 by the surface having an inclination angle of 0° directly enters the photographing lens of the digital camera 16 as a specular reflection component. In the captured or photographed image of the stereoscopic reference 20, the surface having an inclination angle of 0° is a region where reflected light intensity is highest and specular gloss is generated. Accordingly, as the inclination angle of the surface is increased from 0°, the specular reflection component of reflected light of the light source 22 by the inclined surface decreases, and the surface becomes a region where the reflected light intensity is low. From these results, the reflected light intensity of the inclined surface of the stereoscopic reference 20 is analyzed, whereby it is possible to easily estimate the arrangement angle of the light source 22, and thus, it is possible to easily estimate the arrangement of the light source 22, the stereoscopic reference 20, and the digital camera 16.

In the condition determination unit 26, the illumination conditions (illumination geometric conditions) can be determined based on the analyzed arrangement angle information of the light source 22.

Hereinafter, a specific example of the determination by the condition determination unit 26 will be described.

Figure 3:
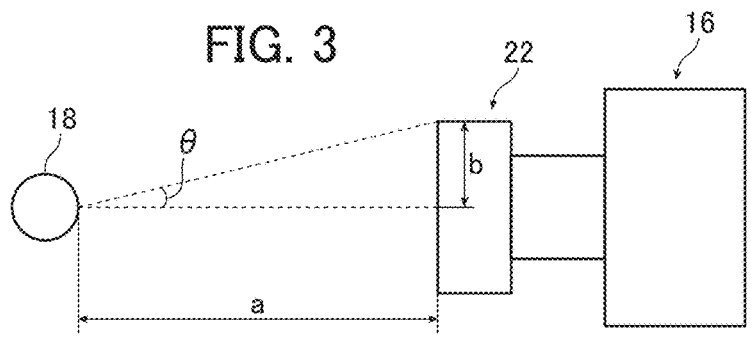
FIG. 3 is a schematic view schematically showing an example of the positional relationship among a digital camera, a light source, and a stereoscopic subject in the photographing unit of the camera system shown in FIG. 2.

FIG. 3 is a schematic view schematically showing an example of the positional relationship among the light source 22 constituted by a ring light flash, the digital camera 16, and the stereoscopic subject 18 for the determination by the condition determination unit 26 when photographing the stereoscopic subject 18 by the ring light flash-equipped digital camera 16.

In the case shown in FIG. 3, various kinds of information described below can be acquired and estimated.

First, as shown in FIG. 3, the distance b between the digital camera 16 (the center of the photographing lens) and the light source 22 (the position of ring light of the ring light flash) can be known from the diameter D of ring light and is given by b=D/2.

Next, as shown in FIG. 3, the distance between the stereoscopic subject 18 and the digital camera 16 can be obtained from the focusing position information of the digital camera 16.

The use of ring light can be known from the on and off information of the ring light flash.

With the use of ring light, it can be estimated that the digital camera 16 is in front of the stereoscopic subject 18.

Further, with the use of ring light, light quality of ring light, such as a color temperature or a spectral distribution, can be estimated.

From the above information, the illumination geometric conditions (illumination angle, illumination distance) and the illumination light quality conditions (the on and off of the flash: flash light source/room lamp) of the illumination conditions shown in FIG. 3 are obtained. Herein, when the flash is on, flash light (ring light) is selected as illumination light quality, and when the flash is off, indoor light is selected as illumination light quality.

In the example shown in FIG. 3, the illumination angle $\theta$ of the illumination geometric conditions can be obtained by a relational expression $\tan \theta = b/a$, and the illumination distance a between the light source 22 and the stereoscopic subject is equal to the distance between the stereoscopic subject 18 and the digital camera 16 as shown in FIG. 3 because of the ring light flash-equipped digital camera 16 and can be obtained from the focusing position information.

Thus, the combination (angle θ, distance a, and the on and off of the flash light source) of the management items of the illumination conditions (illumination geometric conditions and illumination light quality conditions) is determined by the determination of the condition determination unit 26.

That is, in order to select a stereoscopic color profile corresponding to the illumination conditions determined by the condition determination unit 26 from among the stereoscopic color profiles stored in the database 24, for example, the combination (angle θ, distance a, and the on and off of the flash light source) of the management items of the illumination conditions associated with the stereoscopic color profile shown in Table 2 and Table 3 are obtained.

The condition determination unit 26 can determine the above-described illumination conditions, such as the illumination geometric conditions and the illumination light quality conditions, by various methods described below.

Figure 4A:
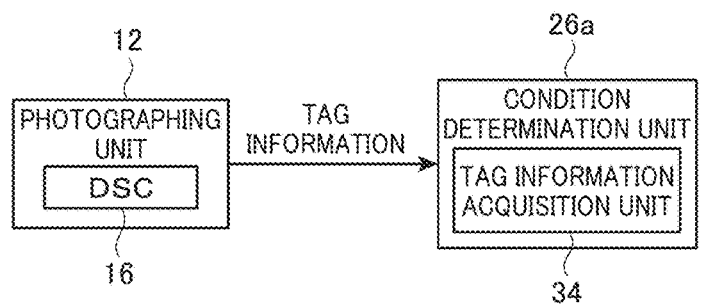

Like a condition determination unit 26a shown in FIG. 4A, when the condition determination unit 26a has a tag information acquisition unit 34 which acquires tag information of a photographed image from the digital camera 16 of the photographing unit 12, as described above, the condition determination unit 26a determines the illumination conditions from the tag information, such as the focusing information or the on and off information of the flash, transmitted from the digital camera 16 and acquired by the tag information acquisition unit 34. For example, in the above-described acquisition methods a) to d) of information of the management items of the illumination conditions and the example shown in FIG. 3, it is preferable that tag information of an image file of the digital camera 16 is acquired in the tag information acquisition unit 34, and the illumination conditions are determined by the condition determination unit 26a.

In the tag information acquisition unit 34 of the condition determination unit 26a, when photographing the stereoscopic subject 18 illuminated by the light source 22 by the photographing unit 12, geometric positional information representing the geometric arrangement relationship of three of the light source 22, the stereoscopic subject 18, and the digital camera 16 for determining the geometric positional relationship among three of the light source 22, the stereoscopic subject 18, and the digital camera 16, the distance (photographing distance) between the stereoscopic subject 18 and the digital camera 16, information regarding the light scattering property, polarization property, spectral distribution, and color temperature of the light source 22, or the like may be acquired as tag information.

Figure 4B:
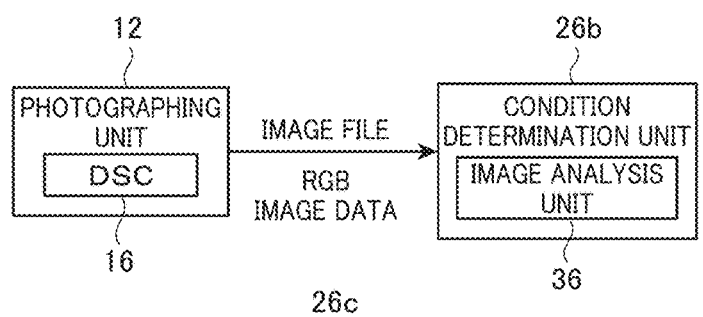

As shown in FIG. 4B, when a condition determination unit 26b has an image analysis unit 36 which receives the image file (RGB image data) of the photographed image from the digital camera 16 of the photographing unit 12 and performs image analysis, as described above, the image analysis unit 36 of the condition determination unit 26b performs image analysis on the image file (RGB image data) of the photographed image received from the digital camera 16 and determines the illumination conditions. For example, in the above-described acquisition methods e) to g) of information of the management items of the illumination conditions, it is preferable that image data of the image file of the digital camera 16 is subjected to image analysis in the image analysis unit 36, and the illumination conditions are determined by the condition determination unit 26b.

Figure 4C:
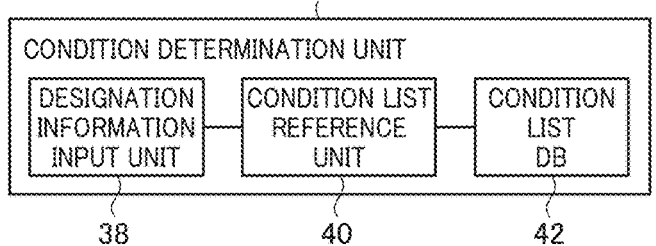

As shown in FIG. 4C, a condition determination unit 26c has a designation information input unit 38 which receives illumination conditions as designation information directly inputted by a human or receives designation information for acquiring the illumination condition inputted by a human, a condition list reference unit 40 which acquires the illumination conditions directly input as designation information as the determined illumination conditions or acquires the input designation information as acquisition condition for acquiring the illumination conditions, and a condition list database (DB) 42 which stores a plurality of illumination conditions according to the designation information or the acquisition condition in the form of a list. In the condition list DB 42, the combination of the illumination geometric conditions of the illumination angle, the illumination distance, and the like, and the illumination light quality conditions may be registered in advance like illumination conditions A, B, and C.

In the condition list DB 42 of the condition determination unit 26c, a list of (the management items and the like of) the illumination conditions corresponding to the designation information inputted from the designation information input unit 38 has been created. In this case, the designation information may be a designation number. The number of the list of (the management items and the like of) the illumination conditions in the condition list DB 42 displayed on a display device (not shown), such as a monitor, is designated and inputted from the designation information input unit 38, whereby the condition list reference unit 40 can acquire the corresponding illumination conditions in the list from the condition list DB 42 and can set the illumination conditions as the illumination conditions determined by the condition determination unit 26c. The designation information inputted from the designation information input unit 38 is not limited to the designation number of the list of the illumination conditions, and any means may be used as long as the corresponding illumination conditions in the list can be designated. For example, the designation information may be information used as the tag information, such as the geometric positional information representing the geometric arrangement relationship among three of the light source 22, the stereoscopic subject 18, and the digital camera 16, information regarding the distance (photographing distance) between the stereoscopic subject 18 and the digital camera 16, information regarding light quality of the light source 22 such as light scattering property, polarization property, spectral distribution, and color temperature, or the like. The combinations of the geometric positional information and information regarding light quality may be registered like combination conditions a, b, and c. In this case, in the condition list DB 42, a list of illumination conditions corresponding to (linked with) such information is stored. In the list of the condition list DB 42, if there are no illumination conditions corresponding to the designation information, the corresponding illumination conditions may be obtained by interpolation or the like from similar or last and next illumination conditions.

Figure 4D:
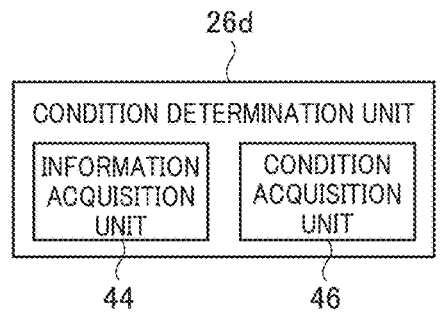

A condition determination unit 26d shown in FIG. 4D is used, for example, when the illumination conditions can be directly acquired as photographing system information in the photographing unit 12 of the camera system 10, or when information for acquiring the illumination conditions, such as the geometric positional information representing the geometric arrangement relationship among three of the light source 22, the stereoscopic subject 18, and the digital camera 16, information regarding the photographing distance, or information regarding the light quality of the light source 22, can be acquired as the photographing system information in the photographing unit 12 of the camera system 10. The condition determination unit 26d has an information acquisition unit 44 which acquires the photographing system information from the camera system 10 or the photographing unit 12, and a condition acquisition unit 46 which acquires the corresponding illumination conditions from the photographing system information acquired by the information acquisition unit 44. Though not shown, as with the condition list database (DB) 42 of the condition determination unit 26c shown in FIG. 4C, the condition determination unit 26d may have a condition list database (DB) which stores a plurality of illumination conditions according to the photographing system information in the form of a list.

In the condition determination unit 26d, the condition acquisition unit 46 obtains the corresponding illumination conditions from the photographing system information acquired by the information acquisition unit 44. A method of obtaining the illumination conditions in the condition acquisition unit 46 is not particularly limited, and the illumination geometric conditions, the illumination light quality conditions, and the like may be calculated from the photographing system information, or when the condition list DB 42 is provided, the illumination conditions corresponding to the acquired photographing system information may be acquired. When acquiring the illumination conditions from the condition list DB, if there are no illumination conditions corresponding to the designation information in the list, the corresponding illumination conditions may be obtained by interpolation or the like from similar or last and next illumination conditions.

The selection unit 28 selects a stereoscopic color profile corresponding to the illumination condition from the database 24, based on the illumination condition at the time of photographing of the stereoscopic subject 18 obtained by the determination of the condition determination unit 26, for example, the illumination geometric condition, the illumination light quality condition, and the like.

For example, as shown in Table 2 and Table 3 described above, when the database 24 stores the stereoscopic color profiles according to the combination (the illumination angle θ, the illumination distance a, and the on and off of the flash) of the management items of the illumination conditions, the selection unit 28 selects a stereoscopic color profile corresponding to the combination (the illumination angle θ, the illumination distance a, and the on and off of the flash) of the management items of the illumination conditions determined by the condition determination unit 26. For example, when the illumination conditions are that the room lamp of the Room A is a fluorescent lamp, the illumination angle θ is 30°, the flash is on, and the illumination distance a is 30 cm, the corresponding stereoscopic color profile P5 is selected from Table 2 in the database 24.

When there is no appropriate stereoscopic color profile corresponding to the illumination conditions, such as the illumination geometric conditions or the illumination light quality conditions, a stereoscopic color profile may be created by interpolation from a plurality of stereoscopic color profiles of close illumination conditions, for example, from a plurality of stereoscopic color profiles corresponding to a plurality of similar illumination conditions, and preferably, last and next illumination conditions.

For example, as shown in Table 2 and Table 3 described above, when there is no stereoscopic color profile corresponding to the distance of 20 cm, an approximate stereoscopic color profile can be created by interpolation from the stereoscopic color profile corresponding to 15 cm and the stereoscopic color profile corresponding to 30 cm.

The color conversion unit 30 performs color conversion of RGB image data of the image of the stereoscopic subject 18 photographed by the photographing unit 12 to colorimetric values (colorimetric image data), for example, XYZ colorimetric values (XYZ image data), based on the stereoscopic color profile selected by the selection unit 28.

The converted colorimetric values obtained through the color conversion by the color conversion unit 30 is not limited to the XYZ colorimetric values (XYZ image data) of the standard color system, and any colorimetric value may be used. For example, an La*b* colorimetric value, an Lu*v* colorimetric value, and the like may be used as the colorimetric values.

The image output unit 32 outputs a colorimetric image, for example, an XYZ colorimetric image of the stereoscopic subject 18 color-converted by the color conversion unit 30.

The color conversion device according to the first embodiment of the invention and the camera system using the color conversion device are basically configured as above.

In the above-described first embodiment, when the stereoscopic reference 20 or the stereoscopic subject 18 such as an actual human tooth is photographed by the digital camera 16, if many specular gloss components are included in the photographed image, a specular gloss region where many specular gloss components are included becomes a high brightness region or a high lightness region. Accordingly, if various analyses including the color conversion by the color conversion device 14 are performed using image data of the photographed image including the high brightness or high lightness region, the accuracy of color prediction of the stereoscopic reference 20 or the stereoscopic subject 18 may be degraded.

In this case, it is preferable that a stereoscopic object composed of a curved surface having various inclination angles or a stereoscopic object composed of a plurality of flat surfaces having various inclination angles such as a polyhedron is used as the stereoscopic reference 20, an analysis region excluding a specular gloss region is set in the photographed image in advance based on the brightness distribution (lightness distribution) of the photographed image of the stereoscopic reference 20, and when analyzing the photographed image of the stereoscopic reference 20 or the stereoscopic subject 18, various analyses including the color conversion are performed in the analysis region set in advance, thereby maintaining the high accuracy of the color prediction without degrading the accuracy thereof.

It is preferable that the setting of the analysis region by use of the stereoscopic reference 20 is performed in the following setting flow.

First, as advance preparation, either or both of the curvature and the inclination angle of the stereoscopic reference 20 are measured in advance. At this time, in the case of the oval stereoscopic reference 20a shown in FIGS. 11A and 11B, it is preferable to measure the curvature of the curved surface or the inclination angle of the surface when the curved surface is viewed discretely. In the case of the polyhedral stereoscopic reference 20b shown in FIG. 11C, it is preferable to measure the inclination angle of each surface.

Next, the reflected light distribution (brightness distribution) of the stereoscopic reference 20 photographed at various angles under conditions close to the photographing conditions is measured.

As described above, in an optical geometric arrangement of the stereoscopic reference 20, the light source 22, and the digital camera 16, when the stereoscopic reference 20 has an inclined surface which becomes a reflection surface configured to reflect emitted light from the light source 22 so as to directly enter the digital camera 16, for example, when the polyhedron has at least a flat surface or a curved surface which becomes the inclined surface, if the inclination angle of the inclined surface of the stereoscopic reference 20 is 0°, as shown in FIG. 12, the reflected light intensity in the inclined surface of the stereoscopic reference 20 having an inclination angle of 0° is highest. As the inclination angle increases, the reflected light intensity decreases.

Next, from the measurement results, that is, from the measurement result of either or both of the curvature and the inclination angle of the stereoscopic reference 20 and the measurement result of the reflected light distribution of the stereoscopic reference 20, a specific range of either or both of the curvature and the inclination angle in which the reflected light intensity is not excessively increased is set as an analysis range, and the set analysis range is registered and stored in the database 24. Needless to say, at the time of creating a stereoscopic color profile for the stereoscopic reference 20, only the photographed image data of the analysis range is preferably used. Thus, the created stereoscopic color profile is stored in the database 24.

For example, in the case of the stereoscopic reference 20 for the stereoscopic subject 18 such as a tooth as shown in FIG. 12, the range of the inclination angle set as the analysis range is preferably −180° to −5° and 5° to 180°, and more preferably, −180° to −10° and 10° to 180°.

Next, in the photographing of the stereoscopic subject 18, the reflected light distribution (brightness distribution) of the captured image of the stereoscopic subject 18 such as a tooth is acquired. For example, as shown in FIG. 13A, in the stereoscopic subject 18, it is assumed that two regions 18*a* and 18*b* are places where specular gloss is generated, and specular reflection is not generated in the remaining region.

Then, the acquired reflected light distribution of the photographed image is compared with the relationship between the specific range of either or both of the curvature and the inclination angle and the reflected light distribution registered in the database 24, and only the portion of either or both of the curvature and the inclination angle designated as the analysis range in advance is set as an analysis region. That is, in a photographed image 48 of the stereoscopic subject 18 shown in FIG. 13B, regions 48*a* and 48*b* corresponding to two specular gloss regions 18*a* and 18*b* of the stereoscopic subject 18 are excluded from the analysis range, and only a hatched region 48*c* is set as the analysis region.

Only RGB image data in the analysis region set as above of the photographed image of the stereoscopic subject 18 is used in the color conversion unit 30. As a result, color prediction can be performed with high accuracy.

In the invention, although the specific range of either or both of the curvature and the inclination angle is set as the analysis range, the invention is not limited thereto. A portion exceeding a specific threshold value (brightness) of the reflected light distribution may be set in advance as a specular gloss component from the measurement result of the reflected light distribution (brightness) of the above-described stereoscopic reference 20 and registered in the database 24, and an analysis region which is the region of the stereoscopic subject 18 and a specific region of the specific threshold value (brightness) or less may be set from the reflected light distribution of the image of the stereoscopic subject 18 such as a tooth or the like obtained in the photographing thereof.

Although the camera system 10 shown in FIG. 1 is configured such that the photographed image of the stereoscopic subject 18 is converted to the colorimetric image using the stereoscopic color profiles defining the conversion relationship between RGB image data of the photographed image of the stereoscopic reference 20 and the reference colorimetric value of the stereoscopic reference 20 according to the illumination conditions (illumination geometric conditions and the illumination light quality conditions) at the time of photographing, and the colorimetric image is output, the present invention is not limited thereto. A camera system may be configured such that the photographed image obtained by photographing the stereoscopic subject 18 using the photographing unit 12 is converted to a colorimetric image using a planar color profile defining the conversion relationship between RGB image data and the colorimetric values and a stereoscopic color correction profile defining the conversion relationship between a reference colorimetric value of an approximate color stereoscopic reference and illumination conditions (illumination geometric conditions and illumination light quality conditions) at the time of photographing of the approximate stereoscopic reference, and the colorimetric image is output.

FIG. 5 is a block diagram schematically showing an example of the configuration of a camera system using a color conversion device according to a second embodiment of the present invention. FIG. 6 is a schematic view schematically showing an example of a photographing unit of the camera system shown in FIG. 5, a stereoscopic subject to be photographed, a planar color chart, and a reference color stereoscopic object.

A camera system 50 shown in FIG. 5 has the same configuration as the camera system 10 shown in FIG. 1, except that a planar color chart 60 and an approximate color stereoscopic reference 62 are used instead of the stereoscopic reference 20, and a database 54, a selection unit 56, and a color conversion unit 58 are respectively used instead of the database 24, the selection unit 28, and the color conversion unit 30, and accordingly, the same constituent elements are represented by the same reference numerals, and detailed description thereof will not be repeated.

As shown in FIG. 5, the camera system 50 has the photographing unit 12 which photographs the stereoscopic subject 18 to acquire image data of three colors, and the color conversion device 52 which color-converts the image data acquired by the photographing unit 12 to colorimetric values.

As shown in FIG. 6, the photographing unit 12 includes the digital camera 16, and the photographing light source 22 which illuminates a subject, such as the stereoscopic subject 18 or the planar color chart 60 and one or more, preferably a plurality of approximate color (or similar color) stereoscopic references 62 as a reference color stereoscopic object, with illumination light at the time of photographing by the digital camera 16.

As shown in FIG. 5, the color conversion device 52 has a database (DB) 54 which stores a plurality of stereoscopic color correction profiles, in which colorimetric values respectively obtained according to a plurality of illumination conditions by the photographing unit 12 are associated with one or more approximate color stereoscopic references 62 assigned with reference colorimetric values in advance, and one planar color profile representing a conversion relationship calculated from RGB image data obtained by photographing a plurality of planar color charts 60 assigned with the reference colorimetric values in advance by the digital camera 16 of the photographing unit 12 and the reference colorimetric values of the planar color charts 60; a condition determination unit 26 which determines an illumination condition for illuminating the stereoscopic subject 18 at the time of photographing by the photographing unit 12; a selection unit 56 which selects a corresponding stereoscopic color correction profile from the database 24 based on the illumination condition at the time of photographing the stereoscopic subject 18; a color conversion unit 58 which color-converts the RGB image data of the image of the stereoscopic subject 18 photographed by the photographing unit 12 to colorimetric values, for example, XYZ colorimetric values based on one planar color profile stored in the database 54 and the stereoscopic color correction profile selected by the selection unit 28; and an image output unit 32 which outputs a colorimetric image, for example, an XYZ colorimetric image of the stereoscopic subject 18 color-converted by the color conversion unit 58.

As with the stereoscopic references 20 shown in FIG. 2, the planar color charts 60 shown in FIG. 6 have a plurality of colors assigned with reference colorimetric values (planar reference colors), preferably, linearly independent three or more different colors, and in the example in the drawing, as with the stereoscopic references 20 shown in FIG. 2, the planar color charts 60 have eight colors assigned with reference colorimetric values. The planar color charts 60 are not particularly limited as long as the planar color charts have a plurality of colors assigned with reference colorimetric values, and planar color charts known in the prior art can be used. However, it is preferable that one color among the plurality of colors is a color (approximate color) similar to that of the stereoscopic subject 18 to be photographed, and it is more preferable that for the reference colorimetric values (planar reference colors) assigned in advance, a color type suitable for the stereoscopic subject 18 is selected.

The approximate colors stereoscopic references (hereinafter, simply referred to as stereoscopic references) 62 are plural but the same as the stereoscopic references 20 shown in FIG. 2, except that the colors assigned with the reference colorimetric values are colors (approximate colors) similar to those of the stereoscopic subject 18 to be photographed, and thus, detailed description thereof will not be repeated.

In this embodiment, the stereoscopic references 62 are photographed along with the stereoscopic subject 18.

The color conversion device 52 is a color conversion device which converts the photographed image of the stereoscopic subject 18 to the colorimetric image using the planar color charts 60 defining the conversion relationship between RGB image data and the colorimetric values and the stereoscopic color correction profiles defining the conversion relationships between the reference colorimetric values of the stereoscopic references 62 and the illumination conditions (the illumination geometric conditions and illumination light quality conditions) at the time of photographing of the stereoscopic references 62, and outputs the colorimetric image.

Although the database 54 of the color conversion device 52 stores a plurality of stereoscopic color correction profiles, in the example shown in the drawing, the database 54 also stores one planar color profile representing the conversion relationship calculated from RGB image data and the reference colorimetric value. In this way, it is preferable that a plurality of stereoscopic color correction profiles and one planar color profile are stored in the same database 54.

However, the planar color profile is one, and is not limited to being stored in the database 54 and may be stored in any memory. Since the planar color profile is used in the color conversion unit 58 described below, it is also preferable for the planar color profile to be stored in a memory in the color conversion unit 58.

In this embodiment, the stereoscopic color correction profiles are created according to the illumination conditions (one or more illumination geometric conditions and/or one or more illumination light quality conditions), for example, the illumination angle (measurement angle) and the like using the stereoscopic references 62 in the same manner as in the first embodiment described above.

The stereoscopic color correction profiles are obtained from the stereoscopic references 62 of colors similar to that of the stereoscopic subject 18, and are the same profiles, except that the colors are similar colors. The number of stereoscopic color correction profiles obtained according to a plurality of illumination conditions (illumination geometric conditions and illumination light quality conditions), that is, the number of one set of stereoscopic color correction profiles may be the same as the number in stereoscopic references 20 shown in FIG. 2. However, in the example shown in the drawing, the number of stereoscopic references 62 to be prepared is three, and can be reduced compared to the number (eight) of stereoscopic references 20 shown in FIG. 2. Accordingly, naturally, the number of sets of stereoscopic color correction profiles stored in the database 54 can be reduced, and the total number of stereoscopic color correction profile can also be reduced.

The selection unit 56 selects a stereoscopic color correction profile corresponding to the illumination condition from the database 54, based on the illumination condition at the time of photographing of the stereoscopic subject 18, for example, the illumination geometric condition, the illumination light quality condition, and the like, which are determined and obtained by the condition determination unit 26.

For example, if the profiles P1 to P24 shown in Table 2 and Table 3 are stereoscopic color correction profiles according to the combination (the illumination angle θ, the illumination distance a, and the on and off of the flash) of the management items of the illumination conditions, the stereoscopic color correction profiles P1 to P24 are stored in the database 54. In this case, the selection unit 56 selects a stereoscopic color profile corresponding to the combination (the illumination angle 9, the illumination distance a, and the on and off of the flash) of the management items of the illumination conditions determined by the condition determination unit 26. For example, when the illumination conditions are that the room lamp of the Room A is a light bulb (incandescent lamp), the illumination angle θ is 0°, the flash is off, and the illumination distance a is 15 cm, it can be said that the corresponding stereoscopic color profile P19 is selected from Table 2 in the database 54.

When there is no appropriate stereoscopic color correction profile corresponding to the illumination condition, such as the illumination geometric condition or the illumination light quality condition, as with the case of the stereoscopic color profile, a stereoscopic color correction profile may be created by interpolation from a plurality of stereoscopic color correction profiles of close illumination conditions, for example, a plurality of stereoscopic color correction profile corresponding to a plurality of similar illumination conditions, preferably, last and next illumination conditions.

For example, as shown in Table 2 and Table 3 described above, when there is no stereoscopic color correction profile corresponding to the distance of 20 cm, an approximate stereoscopic color correction profile can be created by interpolation from the stereoscopic color correction profile corresponding to 15 cm and the stereoscopic color correction profile corresponding to 30 cm.

The color conversion unit 58 color-converts the RGB image data of the image of the stereoscopic subject 18 photographed by the photographing unit 12 to colorimetric values (colorimetric image data), for example, XYZ colorimetric values (XYZ image data), based on one planar color profile stored in the database 54 and the stereoscopic color correction profile selected by the selection unit 56.

Herein, the color conversion unit 58 can perform the color conversion based on the planar color profile and the stereoscopic color correction profile by the following two methods.

A color conversion unit 58a shown in FIG. 7A has a planar color conversion unit 64 which performs planar color conversion of the RGB image data of the image of the stereoscopic subject 18 photographed by the photographing unit 12 to colorimetric values (colorimetric image data) based on the planar color profile, and a stereoscopic color correction unit 66 which performs stereoscopic color correction on the colorimetric values (XYZ colorimetric image data) of the photographed image planar color-converted by the planar color conversion unit 64 based on the stereoscopic color correction profile selected by the selection unit 56. That is, in the color conversion unit 58a, first, in the planar color conversion unit 64, colorimetric conversion is performed on the RGB image data of the photographed image of the stereoscopic subject 18 using the planar color profile based on the planar color charts 60, and then, in the stereoscopic color correction unit 66, color correction as a stereoscopic image is performed on the colorimetric values (colorimetric image data) using the stereoscopic color correction profile according to the illumination conditions for the stereoscopic subject 18, whereby obtaining colorimetric values (colorimetric image data) which are color-converted with excellent accuracy.

A color conversion unit 58b shown in FIG. 7B has a stereoscopic color profile creation unit 68 which creates the same stereoscopic color profile as that used in the camera system 10 of the first embodiment shown in FIG. 1 from the planar color profile created in advance and the stereoscopic color correction profile selected by the selection unit 56, and a stereoscopic color conversion unit 70 which performs stereoscopic color conversion of the RGB image data of the image of the stereoscopic subject 18 photographed by the photographing unit 12 to colorimetric values (colorimetric image data) based on the stereoscopic color profile created by the stereoscopic color profile creation unit 68. That is, in the color conversion unit 58b, first, in the stereoscopic color profile creation unit 68, the stereoscopic color profile is created from the planar color profile based on the planar color charts 60 and the stereoscopic color correction profile selected by the selection unit 56, and then, as with the camera system 10 of the first embodiment shown in FIG. 1, in the stereoscopic color conversion unit 70, color conversion of the RGB image data of the image of the stereoscopic subject 18 photographed by the photographing unit 12 to the colorimetric values (colorimetric image data) is performed at one time. Accordingly, the stereoscopic color conversion unit 70 has the exactly same configuration as the color conversion unit 30 shown in FIG. 1.

The color conversion device according to the second embodiment of the invention and the camera system using the color conversion device are basically configured as above.

In the above-described camera systems 10 and 50 shown in FIGS. 1 and 5, if a stereoscopic color reference (reference color stereoscopic object) having at least one, and preferably, all of semi-transparency, a light scattering property, a color tint of milky white analogous to those of a human tooth is used as the stereoscopic reference 20 or 62, the camera systems can be used as a dental camera system in which a human tooth is the stereoscopic subject 18.

Further, if a stereoscopic color reference (reference color stereoscopic object) having at least one, and preferably all of semi-transparency or non-transparency, a light scattering property, and a color tint of milky white or flesh color analogous to those of human hide or skin is used as the stereoscopic reference 20 or 62, the camera systems 10 and 50 can be used as a skin measuring (diagnostic) camera system in which human hide or skin is the stereoscopic subject 18 by providing therewith a tool for fixing a human face or the like at a predetermined subject distance. In the skin measuring camera system, artificial skin or an artificial breast may be used as the stereoscopic color reference.

Moreover, if a stereoscopic color reference (reference color stereoscopic object) having semi-transparency or non-transparency, a light scattering property, and a color tint analogous to those of a human celom inner wall such as a human esophagus inner wall is used as the stereoscopic reference 20 or 62, the camera systems 10 and 50 can be used as an endoscope camera system in which a human celom inner wall is the stereoscopic subject 18 by applying the photographing unit 12 thereof to an endoscope photographing unit provided with an illumination light guide.

Meanwhile, as described above, in many cases, the stereoscopic subject 18 as a target of the camera systems 10 and 50 of the present invention has a minute stereoscopic structure called a texture on the surface thereof in addition to a stereoscopic structure as a whole. For example, pores or wrinkles of human hide or skin have a stereoscopic structure recessed from the surface of hide (skin), and an edge portion of the recess has a subject angle different from the surface.

Accordingly, by applying a stereoscopic color profile of an angle corresponding to the edge portion of the recess of the minute stereoscopic structure such as the pores and wrinkles detected based on the feature of the texture of the surface, it is possible to perform color reproduction with excellent accuracy for a minute stereoscopic structure of a detail. Thus, by improving color reproducibility of the uneven portion of the detail of the stereoscopic subject 18, it is also possible to obtain feeling of unevenness of the surface.

A stereoscopic color profile which is applied to such a minute stereoscopic structure of a detail may be a stereoscopic color profile applied to the stereoscopic structure as a whole, which is obtained in advance by photographing the stereoscopic reference 20 or 62 corresponding to the stereoscopic structure as a whole by the digital camera 16 under a predetermined illumination condition, or may be a stereoscopic color profile which is corrected so as to correspond to a minute stereoscopic structure based on the above-described stereoscopic color profile applied to the stereoscopic structure as a whole. However, unlike the stereoscopic color profile applied to the stereoscopic structure as a whole, a stereoscopic color profile exclusively for a minute stereoscopic structure, which is obtained in advance by photographing the stereoscopic reference 20 or 62 corresponding to a minute stereoscopic structure by the digital camera 16 under a predetermined illumination condition, is preferable.

In the present invention, in order to appropriately reproduce feeling of unevenness of the detail of the stereoscopic subject 18, the color conversion of the present invention may be performed only for a portion of the stereoscopic subject 18 including an uneven portion as a minute stereoscopic structure. However, it is preferable that the color conversion of the present invention is performed for the stereoscopic structure of the stereoscopic subject 18 as a whole, and the color conversion of the present invention is also performed for a minute stereoscopic structure of an uneven portion as a part of the stereoscopic subject 18.

In the camera systems 10 and 50 shown in FIGS. 1 and 5, although the image data of the stereoscopic subject 18 photographed by the photographing unit 12, preferably, only the image data in the analysis region excluding the specular-gloss region, is converted to colorimetric values by the color conversion unit 30 based on the stereoscopic color profile selected by the selection unit 28 or 56, and the colorimetric values are output to the image output unit 32 as a colorimetric image (for example, XYZ image data), the present invention is not limited thereto, and in addition to the colorimetric image, gloss feeling of the stereoscopic subject 18 may be obtained and output as a predetermined index (for example, a numerical value).

FIGS. 8 and 9 are block diagrams schematically showing examples of the configuration of a camera system using a color conversion device according to third and fourth embodiments of the present invention, respectively.

A camera system 10a shown in FIG. 8 has the same configuration as the camera system 10 shown in FIG. 1, except that a gloss determination unit 72 is provided between the color conversion unit 30 and the image output unit 32, and a camera system 50a shown in FIG. 9 has the same configuration as the camera system 50 shown in FIG. 5, except that a gloss determination unit 72 is provided between the color conversion unit 58 and the image output unit 32. Accordingly, the same constituent elements as those of the camera systems 10 and 50 are represented by the same reference numerals, and detailed description thereof will not be repeated.

As shown in FIG. 8, the camera system 10a has the photographing unit 12 which photographs the stereoscopic subject 18 to acquire image data of three colors, and a color conversion device 14a which color-converts the image data acquired by the photographing unit 12 to colorimetric values.

The color conversion device 14a shown in FIG. 8 includes the database (DB) 24, the condition determination unit 26, the selection unit 28, the color conversion unit 30, a gloss determination unit 72, and the image output unit 32.

Herein, the photographing unit 12 and the database (DB) 24, the condition determination unit 26, the selection unit 28, and the color conversion unit 30 of the color conversion device 14a in the camera system 10a shown in FIG. 8 are the same as the photographing unit 12 and the database (DB) 24, the condition determination unit 26, the selection unit 28, and the color conversion unit 30 of the color conversion device 14 in the camera system 10 shown in FIG. 1, and thus, description thereof will not be repeated.

As shown in FIG. 9, the camera system 50a has the photographing unit 12 which photographs the stereoscopic subject 18 to acquire image data of three colors, and a color conversion device 52a which color-converts the image data acquired by the photographing unit 12 to colorimetric values.

The color conversion device 52a shown in FIG. 9 includes the database (DB) 54, the condition determination unit 26, the selection unit 56, the color conversion unit 58, the gloss determination unit 72, and the image output unit 32.

Herein, the photographing unit 12 and the database (DB) 54, the condition determination unit 26, the selection unit 56, and the color conversion unit 58 of the color conversion device 52a in the camera system 50a shown in FIG. 9 are the same as the photographing unit 12 and the database (DB) 54, the condition determination unit 26, the selection unit 56, and the color conversion unit 58 of the color conversion device 52 in the camera system 50 shown in FIG. 5, and thus, description thereof will not be repeated.

Each of the gloss determination units 72 shown in FIGS. 8 and 9 receives the colorimetric image data (colorimetric values) of the colorimetric image (for example, an XYZ colorimetric image) of the stereoscopic subject 18 color-converted by the color conversion units 30 or 58, and obtains gloss feeling of the stereoscopic subject 18 based on the colorimetric image data.

The image output unit 32 outputs the gloss feeling obtained by the gloss determination unit 72 along with the colorimetric image (XYZ colorimetric image) obtained by the color conversion unit 30 or 58.

There are two major factors, that is, gloss factors for determining the gloss feeling of the stereoscopic subject 18 obtained by the gloss determination unit 72. The first gloss factor is a reflectance of the subject, that is, lightness of the subject itself, and the second gloss factor is clarity of a reflected image from an ambient environment, for example, clarity of a reflected image of a light source.

Lightness (first factor) can be obtained from the colorimetric image data (XYZ) of the XYZ colorimetric image. That is, brightness (lightness) can be determined by a brightness Y value, or an L* value calculated from the colorimetric image data (XYZ).

Clarity of a reflected image (second factor) can be determined from the clearness (clarity) of the contour of the reflected image of the light source imaged on the stereoscopic subject 18. It can be determined that, if the contour is sharp, gloss feeling is high, and if the contour is blurred, gloss feeling is low. For example, in a simple example, as shown in FIGS. 10A and 10B, when a brightness (Y value) image of the stereoscopic subject 18 is ternarized to three regions of a light source reflected image region 74 which has brightness equal to or more than predetermined first brightness (Y1), a non-reflected image region 76 which has brightness equal to or less than predetermined second brightness (Y2) which is smaller than the first brightness (Y1) and in which the light source is not imaged, and an intermediate blur region 78 which has brightness less than the first brightness (Y1) and greater than the second brightness (Y2) (Y1>Y>Y2), it is determined that, if the size (region width) of the intermediate blur region 78 is narrow (small), gloss feeling is high, and if the size is wide (great), gloss feeling is low.

The position at which the reflected image of the light source is imaged needs to be separated from a principal portion of the stereoscopic subject 18. When it is difficult to separate the position, at which the reflected image of the light source is imaged, from the principal portion of the stereoscopic subject 18 due to the photographing limitations, photographing capable of imaging the reflected image of the light source is preferably performed separately from the photographing of the colorimetric image.

In regard to gloss feeling, lightness, for example, the maximum value of the Y value or the L* value and the maximum value of clarity of a reflected image (the minimum value of the region width of the intermediate blur region 78) are obtained in advance for the stereoscopic subject 18, and gloss feeling can be expressed by a combination of lightness (Y value, L* value) and clarity of a reflected image (the region width of the intermediate blur region 78) of the photographed stereoscopic subject 18 with respect to the combination of the maximum value of lightness and the maximum value of clarity of a reflected image. Of course, both combinations may be indexed as one numerical value and obtained as a numerical index.

In the present invention, the processing flow of the color conversion device 14 of the camera system 10 shown in FIG. 1 can be performed as a color conversion method.

That is, a color conversion method according to a first embodiment of the invention can be performed by creating a database which stores a plurality of stereoscopic color profiles, in which a plurality of conversion relationships calculated from image data obtained by photographing a plurality of reference color stereoscopic objects assigned with reference colorimetric values in advance and the reference colorimetric values corresponding to the image data are associated with a plurality of illumination conditions including illumination geometric conditions in the photographing of the reference color stereoscopic objects; photographing a stereoscopic subject to acquire image data; based on an illumination condition at the time of photographing of the stereoscopic subject, selecting a stereoscopic color profile corresponding to the illumination condition from among the plurality of stereoscopic color profiles stored in the database; and performing color conversion from the image data of a photographed image of the photographed stereoscopic subject to colorimetric values (colorimetric image data) based on the selected stereoscopic color profile.

All processing other than the above-described processing performed by the color conversion device 14 of the camera system 10 shown in FIG. 1 can be performed as a color conversion method.

Further, in the present invention, the entire processing flow of the color conversion device 14a of the camera system 10a shown in FIG. 8 can be performed as a color conversion method.

In the present invention, the processing flow of the color conversion device 52 of the camera system 50 shown in FIG. 5 can be performed as a color conversion method.

That is, a color conversion method according to a second embodiment of the present invention can be performed by creating a database which stores a plurality of stereoscopic color correction profiles, in which a plurality of illumination conditions including illumination geometric conditions at the time of photographing are associated with reference color stereoscopic objects assigned with reference colorimetric values in advance of one or more colors of similar colors of the stereoscopic subject; photographing the stereoscopic subject to acquire image data; selecting a corresponding stereoscopic color correction profile from among the plurality of stereoscopic color correction profiles stored in the database based on an illumination condition at the time of photographing of the stereoscopic subject; and performing color conversion from the image data of a photographed image of the photographed stereoscopic subject to colorimetric values (colorimetric image data), based on a conversion relationship calculated from image data obtained by photographing a plurality of planar color charts assigned with reference colorimetric values in advance and the reference colorimetric values, and the selected stereoscopic color correction profile.

All processing other than the above-described processing performed by the color conversion device 52 of the camera system 50 shown in FIG. 5 can be performed as a color conversion method.

Further, in the present invention, the entire processing flow of the color conversion device 52a of the camera system 50a shown in FIG. 9 can be performed as a color conversion method.

Each color conversion method described above can be performed on a computer by executing a color conversion program.

For example, the color conversion program of the present invention has procedures causing a computer, specifically, a CPU thereof to execute the respective steps of each color conversion method described above. A program including the procedures may be constructed as a single program module or a plurality of program modules.

The color conversion program having the procedures executed by the computer may be stored in a memory (storage device) of a computer or a server, or may be stored in a recording medium, and the program is read from a memory or a recording medium by the computer (CPU) in which the program is stored or another computer at the time of execution. Therefore, the present invention may be embodied as a computer-readable memory or recording medium having recorded thereon the color conversion program causing a computer to execute the color conversion method.

Although the camera system, the dental camera system, the skin measuring (diagnostic) camera system, the color conversion device, the color conversion method, the color conversion program, and the storage medium according to the present invention have been described in detail, the present invention is not limited to the foregoing embodiments, and may be improved or modified in various ways without departing from the gist of the present invention.

What is claimed is:

1. A camera system comprising:
   a photographing unit which photographs a stereoscopic subject to acquire first image data;
   a database which stores a plurality of stereoscopic color profiles, in which a plurality of conversion relationships calculated from second image data obtained by photographing a plurality of reference color stereoscopic objects assigned with reference colorimetric values in advance by the photographing unit and the reference colorimetric values corresponding to the second image data are associated with a plurality of illumination conditions including illumination geometric conditions in the photographing of the reference color stereoscopic objects;
   a selection unit which, based on an illumination condition at the time of photographing of the stereoscopic subject, selects a stereoscopic color profile corresponding to the illumination condition from among the plurality of stereoscopic color profiles stored in the database; and
   a color conversion unit which performs color conversion from the first image data of a photographed image of the stereoscopic subject photographed by the photographing unit to colorimetric values, based on the stereoscopic color profile selected by the selection unit.

2. The camera system according to claim 1,
   wherein the plurality of reference color stereoscopic objects are reference color stereoscopic objects of three or more colors, and
   the plurality of stereoscopic color profiles are respectively created according to the plurality of illumination conditions for the respective reference color stereoscopic objects of three or more colors.

3. The camera system according to claim 1,
   wherein the reference color stereoscopic objects have at least one of a curved surface, a stereoscopic shape, an uneven surface shape, and a layer structure which are identical or analogous to those of the stereoscopic subject, and a polyhedron composed of a plurality of flat surfaces having different inclinations or a curved surface, and are stereoscopic objects made of a material analogous to the stereoscopic subject.

4. The camera system according to claim 1,
wherein the reference color stereoscopic objects include reference color stereoscopic objects having at least one of semi-transparency, non-transparency, a light scattering property, and a color tint of milky white and/or flesh color which are analogous to those of the stereoscopic subject.

5. The camera system according to claim 1,
wherein the photographing unit includes a digital camera, and
an illumination geometric condition includes geometric positional information of three of a light source, the digital camera, and the stereoscopic subject or the reference color stereoscopic objects.

6. The camera system according to claim 5,
wherein each of the reference color stereoscopic objects is a polyhedron composed of a plurality of flat surfaces having different inclinations or a curved surface, and
arrangement angle information of the light source is analyzed based on a flat surface or a curved surface having high reflection brightness of the polyhedron and is set as the illumination geometric condition.

7. The camera system according to claim 6,
Wherein, in an optical geometric arrangement between the digital camera and the light source, the polyhedron has at least a flat surface or a curved surface which becomes a reflection surface configured to reflect emitted light from the light source so as to directly enter the digital camera.

8. The camera system according to claim 5,
wherein the illumination geometric condition is at least one of an illumination angle and an illumination distance of the stereoscopic subject or the reference color stereoscopic objects by the light source.

9. The camera system according to claim 1, further comprising:
a condition determination unit which determines the illumination condition at the time of photographing of the stereoscopic subject,
wherein the selection unit selects a stereoscopic color profile or a stereoscopic color correction profile corresponding to the illumination condition from the database, based on the illumination condition determined by the condition determination unit.

10. The camera system according to claim 9,
wherein the illumination condition further includes an illumination light quality condition of illumination light at the time of photographing, in addition to the illumination geometric condition, and
the condition determination unit determines the illumination geometric condition and the illumination light quality condition as the illumination condition.

11. The camera system according to claim 9,
wherein the condition determination unit includes at least one of an incidental information acquisition unit which acquires incidental information at the time of photographing of the stereoscopic subject from the photographing unit, an image analysis unit which performs image analysis of the photographed image of the stereoscopic subject, and a condition list reference unit which is provided with a determination condition combination list set in advance, and determines the illumination condition from at least one of the incidental information acquired by the incidental information acquisition unit, an analysis result by the image analysis unit, and a selection result in the determination condition combination list of the condition list reference unit.

12. The camera system according to claim 1, further comprising:
a gloss determination unit which determines gloss feeling of the stereoscopic subject, based on the colorimetric values of the photographed image of the stereoscopic subject color-converted by the color conversion unit.

13. The camera system according to claim 12,
wherein the gloss determination unit determines gloss feeling based on lightness obtained from the colorimetric values of the photographed image of the stereoscopic subject and clarity of a reflected image of a light source imaged on the stereoscopic subject.

14. The camera system according to claim 1,
wherein each of the reference color stereoscopic objects is a polyhedron composed of a plurality of flat surfaces having different inclinations or a curved surface,
the database further stores, as an analysis range, either or both of an inclination angle of a specific flat surface and a curvature of a specific curved surface which are set from a measurement result of either or both of an inclination angle of each flat surface and a curvature of the curved surface of the polyhedron and a measurement result of reflected light intensity (brightness) of the polyhedron photographed under photographing conditions of the stereoscopic subject by the photographing unit or similar photographing conditions,
only a portion having either or both of an inclination angle of the flat surface and a curvature of the curved surface designated in advance within the analysis range stored in the database is set as an analysis region from a reflected light distribution obtained from the photographed image of the stereoscopic subject photographed by the photographing unit, and
the color conversion unit performs color conversion using the first image data in the analysis region of the photographed image of the stereoscopic subject.

15. A dental camera system comprising:
the camera system according to claim 1,
wherein the stereoscopic subject is a human tooth, and
the reference color stereoscopic objects have semi-transparency, a light scattering property, and a color tint of milky white which are analogous to those of the human tooth.

16. A skin measuring camera system comprising:
the camera system according to claim 1,
wherein the stereoscopic subject is human skin, and
the reference color stereoscopic objects have at least one of semi-transparency or non-transparency, a light scattering property, and a color tint of milky white or flesh color which are analogous to those of the human skin.

17. A camera system comprising:
a photographing unit which photographs a stereoscopic subject to acquire first image data;
a database which stores a plurality of stereoscopic color correction profiles, in which a plurality of illumination conditions including illumination geometric conditions at the time of photographing by the photographing unit are associated with reference color stereoscopic objects assigned with reference colorimetric values in advance of one or more colors of similar colors of the stereoscopic subject;

a selection unit which selects a corresponding stereoscopic color correction profile from among the plurality of stereoscopic color correction profiles stored in the database, based on an illumination condition at the time of photographing of the stereoscopic subject; and a color conversion unit which performs color conversion from the first image data of a photographed image of the stereoscopic subject photographed by the photographing unit to colorimetric values, based on a conversion relationship calculated from second image data obtained by photographing a plurality of planar color charts assigned with reference colorimetric values in advance and the reference colorimetric values, and the stereoscopic color correction profile selected by the selection unit.

18. The camera system according to claim 17, wherein the reference color stereoscopic objects of one or more colors is a reference color stereoscopic object of one color of the similar color of the stereoscopic subject, the plurality of stereoscopic color correction profiles are respectively created according to the plurality of illumination conditions for the reference color stereoscopic object of one color, and the plurality of planar color charts are planar color charts of three or more colors.

19. The camera system according to claim 17, wherein the conversion relationship is a planar color profile, and the color conversion unit performs color conversion of the first image data of the photographed image to intermediate colorimetric values of the photographed image using the planar color profile, and performs color correction of the intermediate colorimetric values of the photographed image color-converted using the selected stereoscopic color correction profile to create the colorimetric values of the photographed image.

20. The camera system according to claim 17, wherein the conversion relationship is a planar color profile, and the color conversion unit creates a stereoscopic color profile using the planar color profile and the selected stereoscopic color correction profile, and performs color conversion from the first image data of the photographed image of the stereoscopic subject to the colorimetric values of the photographed image based on the created stereoscopic color profile.

21. The camera system according to claim 17, further comprising:

a gloss determination unit which determines gloss feeling of the stereoscopic subject based on the colorimetric values of the photographed image of the stereoscopic subject color-converted by the color conversion unit.

22. A dental camera system comprising:
the camera system according to claim 17,
wherein the stereoscopic subject is a human tooth, and
the reference color stereoscopic objects have semi-transparency, a light scattering property, and a color tint of milky white which are analogous to those of the human tooth.

23. A skin measuring camera system comprising:
the camera system according to claim 17,
wherein the stereoscopic subject is human skin, and
the reference color stereoscopic objects have at least one of semi-transparency or non-transparency, a light scattering property, and a color tint of milky white or flesh color which are analogous to those of the human skin.

24. A color conversion device comprising:
a database which stores a plurality of stereoscopic color profiles, in which a plurality of conversion relationships calculated from second image data obtained by photographing a plurality of reference color stereoscopic objects assigned with reference colorimetric values in advance and the reference colorimetric values corresponding to the second image data are associated with a plurality of illumination conditions including illumination geometric conditions in the photographing of the reference color stereoscopic objects;

a selection unit which, based on an illumination condition at the time of photographing of the stereoscopic subject, selects a stereoscopic color profile corresponding to the illumination condition from among the plurality of stereoscopic color profiles stored in the database; and a color conversion unit which performs color conversion from first image data of a photographed image of the stereoscopic subject to colorimetric values, based on the stereoscopic color profile selected by the selection unit.

25. A color conversion method using the color conversion device according to claim 24 and comprising:

creating a database which stores a plurality of stereoscopic color profiles, in which a plurality of conversion relationships calculated from second image data obtained by photographing a plurality of reference color stereoscopic objects assigned with reference colorimetric values in advance and the reference colorimetric values corresponding to the second image data are associated with a plurality of illumination conditions including illumination geometric conditions in the photographing of the reference color stereoscopic objects;

photographing a stereoscopic subject to acquire first image data;

based on an illumination condition at the time of photographing of the stereoscopic subject, selecting a stereoscopic color profile corresponding to the illumination condition from among the plurality of stereoscopic color profiles stored in the database; and performing color conversion from the first image data of a photographed image of the stereoscopic subject to colorimetric values, based on the selected stereoscopic color profile.

26. A non-transitory computer-readable memory or a non-transitory computer-readable recording medium in which is stored a color conversion program which causes a computer to execute the respective steps of the color conversion method according to claim 25 as a procedure.

27. A color conversion device comprising:
a database which stores a plurality of stereoscopic color correction profiles, in which a plurality of illumination conditions including illumination geometric conditions at the time of photographing are associated with reference color stereoscopic objects assigned with reference colorimetric values in advance of one or more colors of similar colors of the stereoscopic subject;

a selection unit which selects a corresponding stereoscopic color correction profile from among the plurality of stereoscopic color correction profiles stored in the database based on an illumination condition at the time of photographing of the stereoscopic subject; and a color conversion unit which performs color conversion from first image data of a photographed image of the stereoscopic subject to colorimetric values, based on a conversion relationship calculated from second image data obtained by photographing a plurality of planar color charts assigned with reference colorimetric values in advance and the reference colorimetric values, and the stereoscopic color correction profile selected by the selection unit.

28. A color conversion method using the color conversion device according to claim 27 and comprising:

creating a database which stores a plurality of stereoscopic color correction profiles, in which a plurality of illumination conditions including illumination geometric conditions at the time of photographing are associated with reference color stereoscopic objects assigned with reference colorimetric values in advance of one or more colors of similar colors of the stereoscopic subject;

photographing the stereoscopic subject to acquire first image data;

selecting a corresponding stereoscopic color correction profile from among the plurality of stereoscopic color correction profiles stored in the database, based on an illumination condition at the time of photographing of the stereoscopic subject; and performing color conversion from the first image data of a photographed image of the stereoscopic subject to colorimetric values, based on a conversion relationship calculated from second image data obtained by photographing a plurality of planar color charts assigned with reference colorimetric values in advance and the reference colorimetric values, and the selected stereoscopic color correction profile.

29. A non-transitory computer-readable memory or a non-transitory computer-readable recording medium in which is stored a color conversion program which causes a computer to execute the respective steps of the color conversion method according to claim 28 as a procedure.

* * * * *